United States Patent
Wasik et al.

(10) Patent No.: US 9,255,279 B2
(45) Date of Patent: Feb. 9, 2016

(54) ANAPLASTIC LYMPHOMA KINASE (ALK) AS AN ONCOGENE CAPABLE OF TRANSFORMING NORMAL HUMAN CELLS

(71) Applicant: The Trustees of the University of Pennsylvania, Philadelphia, PA (US)

(72) Inventors: Mariusz Wasik, Ardmore, PA (US); James L. Riley, Downingtown, PA (US); Qian Zhang, Philadelphia, PA (US); Fang Wei, Drexel Hill, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/197,829

(22) Filed: Mar. 5, 2014

(65) Prior Publication Data

US 2015/0031856 A1    Jan. 29, 2015

Related U.S. Application Data

(60) Provisional application No. 61/774,770, filed on Mar. 8, 2013.

(51) Int. Cl.
*C12N 5/00* (2006.01)
*C12N 5/071* (2010.01)
*C12N 15/85* (2006.01)
*G01N 33/50* (2006.01)
*C12N 15/113* (2010.01)

(52) U.S. Cl.
CPC ............ *C12N 15/85* (2013.01); *G01N 33/5011* (2013.01); *A01K 2207/12* (2013.01); *A01K 2267/0331* (2013.01); *C12N 15/1137* (2013.01); *C12N 2310/14* (2013.01); *G01N 2333/91205* (2013.01)

(58) Field of Classification Search
None
See application file for complete search history.

(56) References Cited

PUBLICATIONS

Chiarle, R. et al., "NPM-ALK Transgenic Mice Spontaneously Develop T-Cell Lymphomas and Plasma Cell Tumors," Blood, 2003, pp. 1919-1927, vol. 101, No. 5.
Elenbaas, B. et al., "Human Breast Cancer Cells Generated by Oncogenic Transformation of Primary Mammary Epithelial Cells," Genes & Development, 2001, pp. 50-65, vol. 15.
Gambacorti-Passerini, C. et al., "Crizotinib in Anaplastic Large-Cell Lymphoma," The New England Journal of Medicine, 2011, pp. 775-776, vol. 364, No. 8.
Hahn, W.C. et al.,"Creation of Human Tumour Cells with Defined Genetic Elements," Nature, 1999, pp. 464-468, vol. 400.
Ince, T.A. et al., "Transformation of Different Human Breast Epithelial Cell Types Leads to Distinct Tumor Phenotypes," Cancer Cell, 2007, pp. 160-170, vol. 12.
Kuefer, M.U. et al., "Retrovirus-Mediated Gene Transfer of NPM-ALK Causes Lymphoid Malignancy in Mice," Blood, 1997, pp. 2901-2910, vol. 90, No. 8.
Kwak, E.L. et al., "Anaplastic Lymphoma Kinase Inhibition in Non-Small-Cell Lung Cancer," The New England Journal of Medicine, 2010, pp. 1693-1703, vol. 363, No. 18.
Li, R. et al., "Development of Anaplastic Lymphoma Kinase (ALK) Small-Molecule Inhibitors for Cancer Therapy," Med. Res. Rev., 2008, pp. 372-412, vol. 28, No. 3.
Marzec, M. et al., "Oncogenic Tyrosine Kinase NPM/ALK Induces Activation of the Rapamycin-Sensitive mTOR Signaling Pathway," Oncogene, 2007, pp. 5606-5614, vol. 26.
Matsuyama, H. et al., "miR-135b NPM-ALK-Driven Oncogenicity and Renders IL-17-Producing Immunophenotype to Anaplastic Large Cell Lymphoma," Blood, 2011, pp. 6881-6892, vol. 118, No. 26.
Tabbo, F. et al., "ALK Signaling and Target Therapy in Anaplastic Large Cell Lymphoma," Frontiers in Oncology, 2012, pp. 1-12, vol. 2, Article 41.
Vincente-Duenas, C. et al., "Expression of MALT1 Oncogene in Hematopoietic Stem/Progenitor Cells Recapitulates the Pathogenesis of Human Lymphoma in Mice," PNAS, 2012, pp. 10534-10539, vol. 109, No. 26.
Wasik, M.A. et al., "Anaplastic Lymphoma Kinase (ALK)-Induced Malignancies: Novel Mechanisms of Cell Transformation and Potential Therapeutic Approaches," Seminars in Oncology, 2009, pp. S27-S35, vol. 36, No. 2, Suppl. 1.
Young, L.C. et al., "Fusion Tyrosine Kinase NPM-ALK Deregulates MSH2 and Suppresses DNA Mismatch Repair Function," The Amercian Journal of Pathology, 2011, pp. 411-421, vol. 179, No. 1.
Zamo, A. et al., "Anaplastic Lymphoma Kinase (ALK) Activates Stat3 and Protects Hematopoietic Cells from Cell Death," Oncogene, 2002, pp. 1038-1047, vol. 21.
Zhang, Q. et al., "Multilevel Dysregulation of STAT3 Activation in Anaplastic Lymphoma Kinase-Positive T/Null-Cell Lymphoma," The Journal of Immunology, 2002, pp. 466-474, vol. 168.
Zhang, Q. et al., "The Potent Oncogene NPM-ALK Mediates Malignant Transformation of Normal Human CD4+ AT Lymphocytes," The American Journal of Pathology, 2013, pp. 1971-1980, vol. 183, No. 6.

*Primary Examiner* — Doug Schultz
(74) *Attorney, Agent, or Firm* — Saul Ewing LLP; Kathryn Doyle

(57) ABSTRACT

The present invention provides compositions and methods for transforming primary mammalian cells using an oncogenic form of ALK wherein the transformed cells display features of that of a corresponding tumor cell isolated from a cancer subject. The invention also provides a method for immortalizing normal CD4+ T lymphocytes with a lymphoma-characteristic form of ALK such as NPM-ALK.

3 Claims, 20 Drawing Sheets

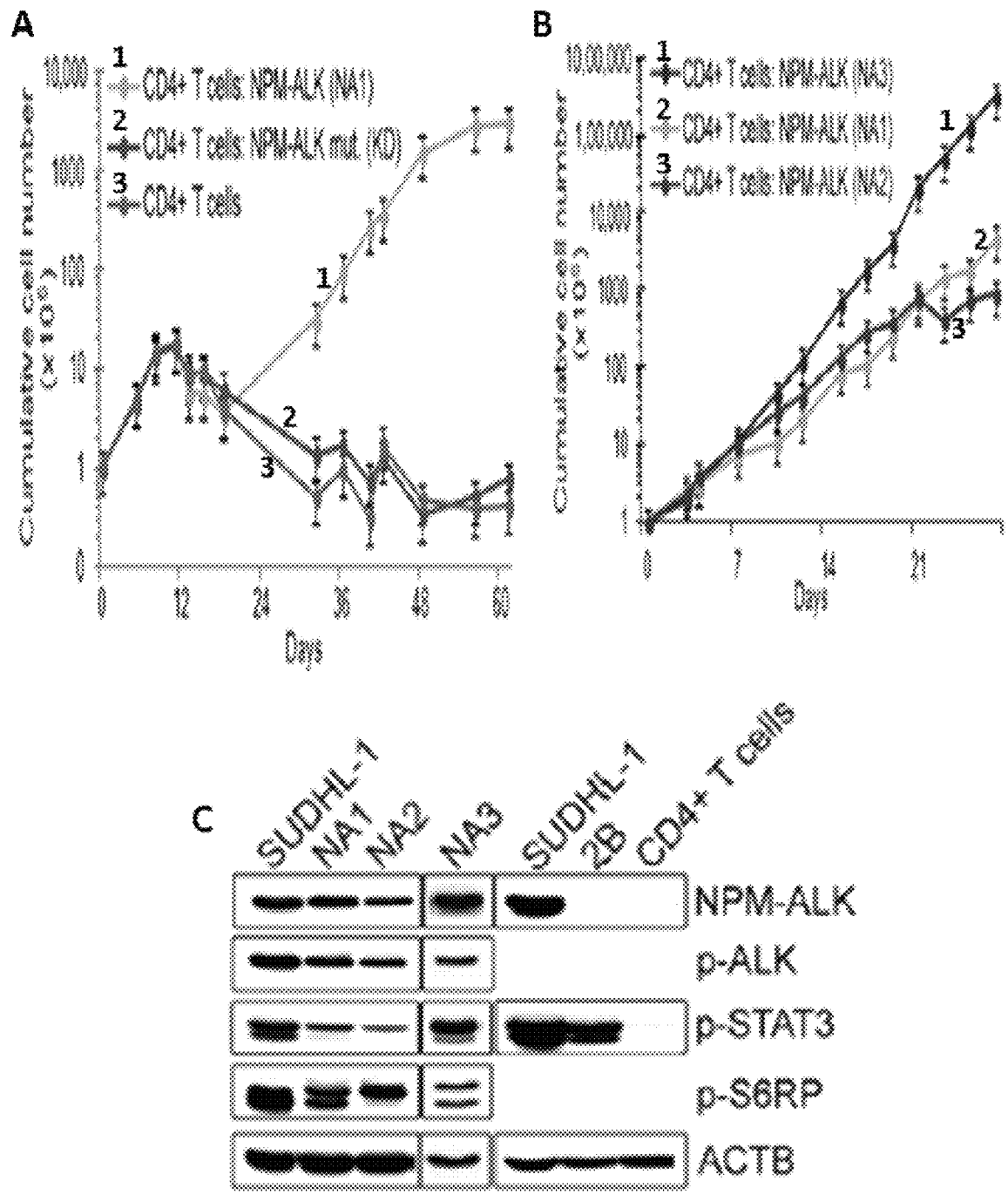
FIG. 1 A-C

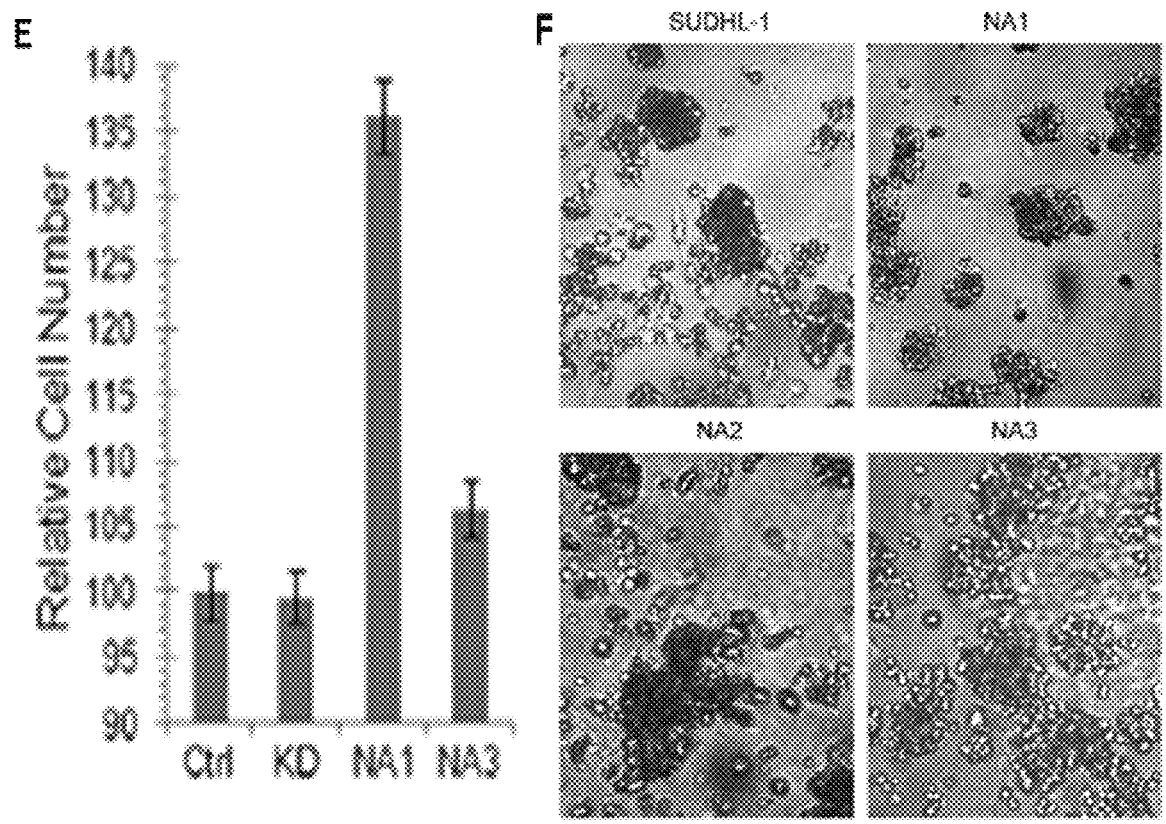
FIG. 1 E-F

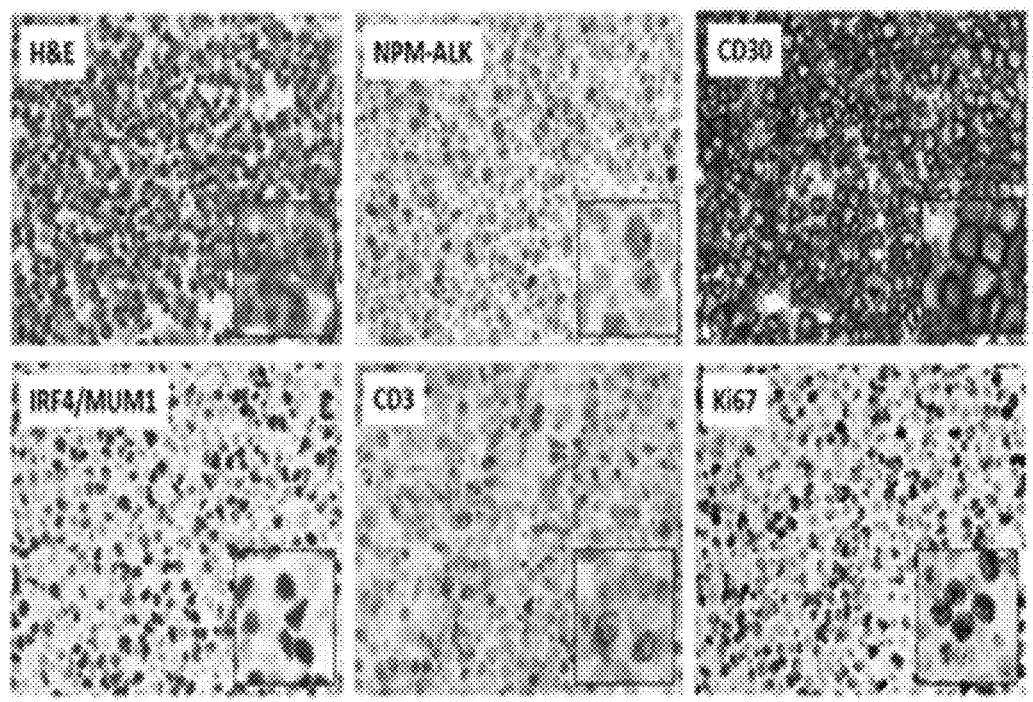
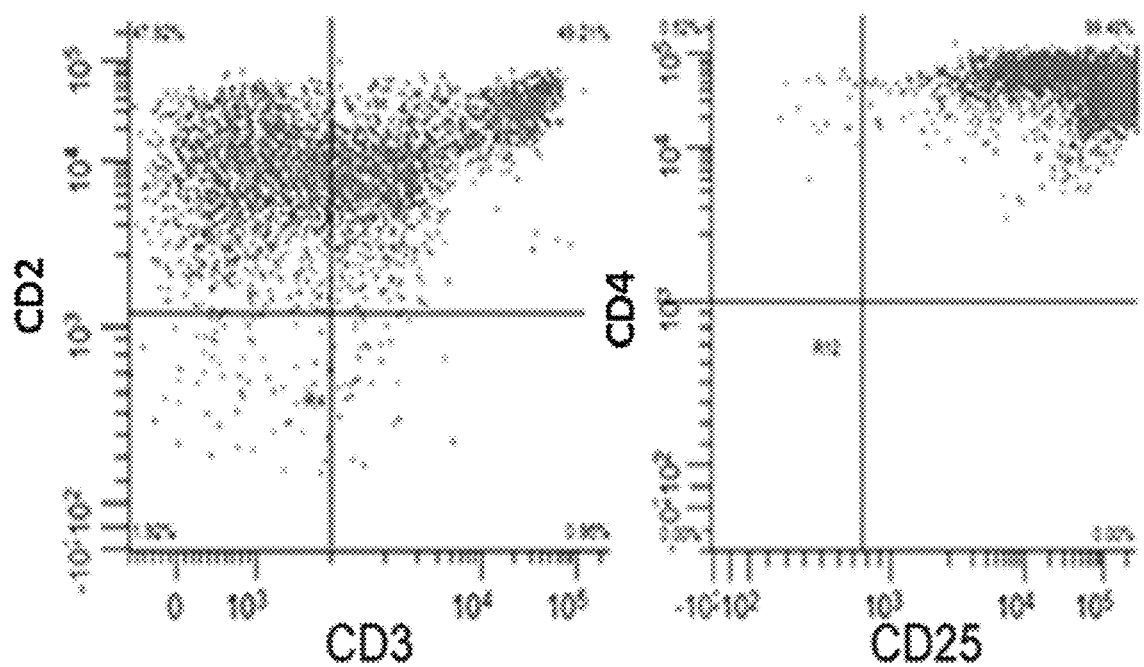
FIG. 2 A-B

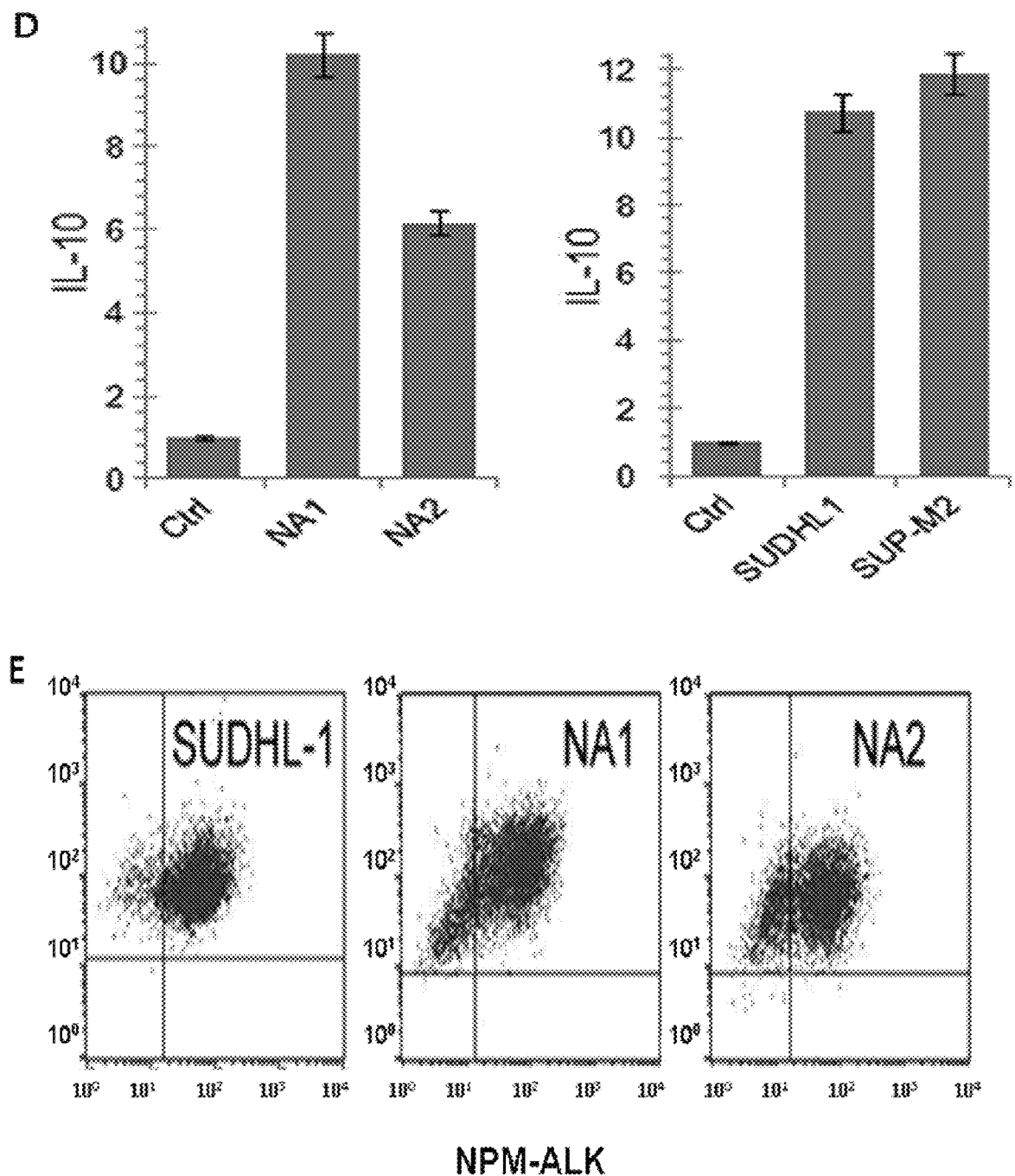
FIG. 2 D-E

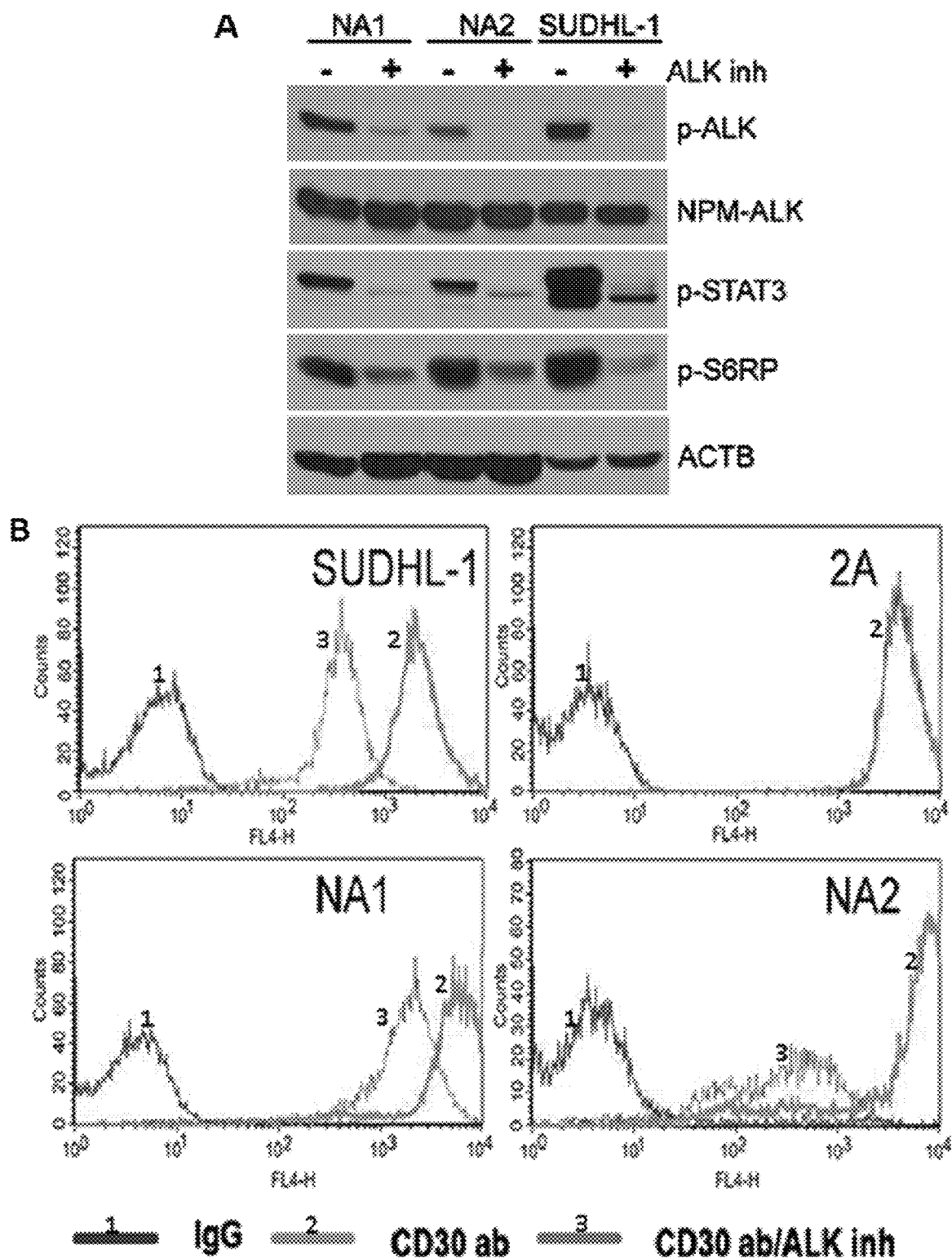
FIG. 3 A-B

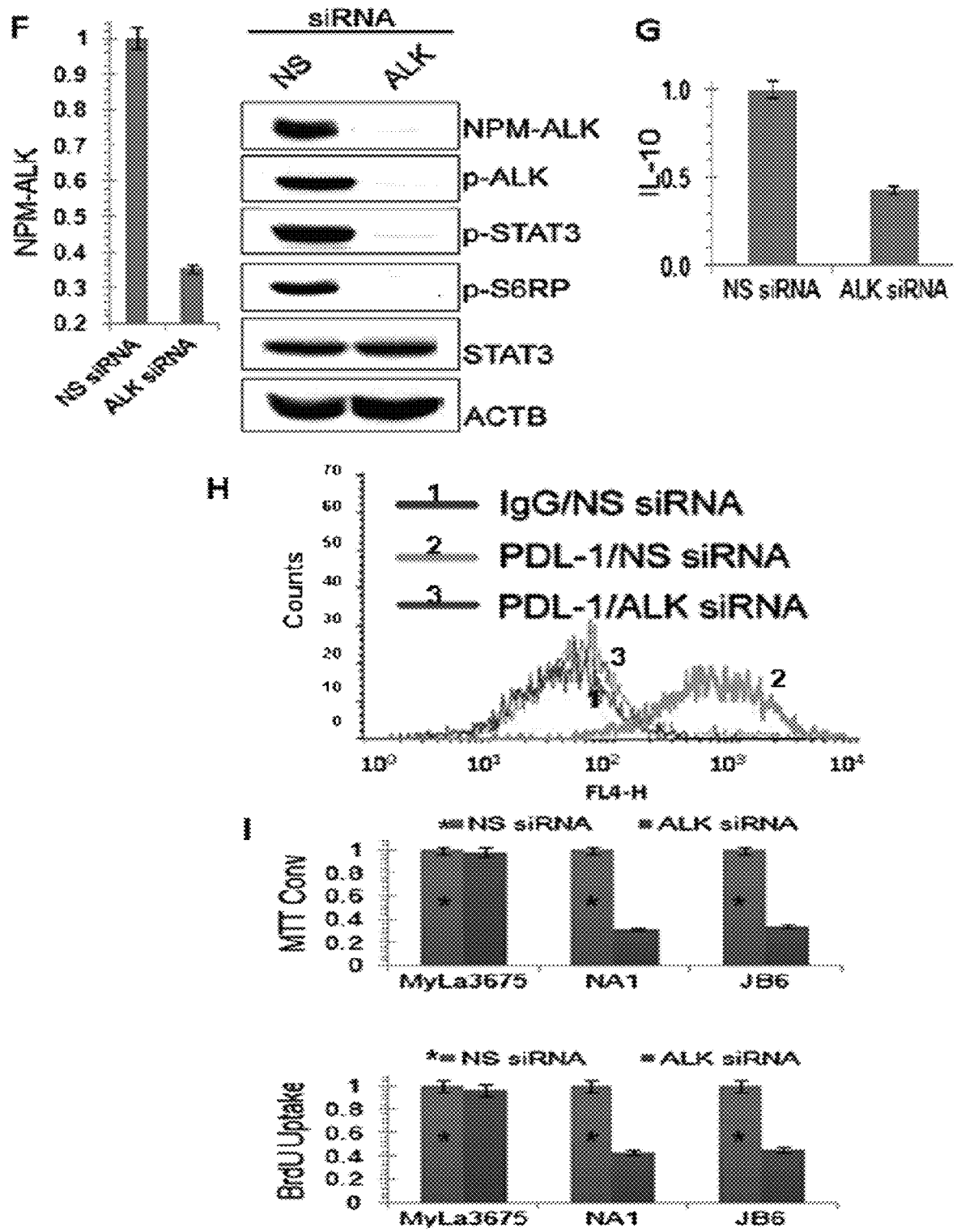
FIG. 3 F-I

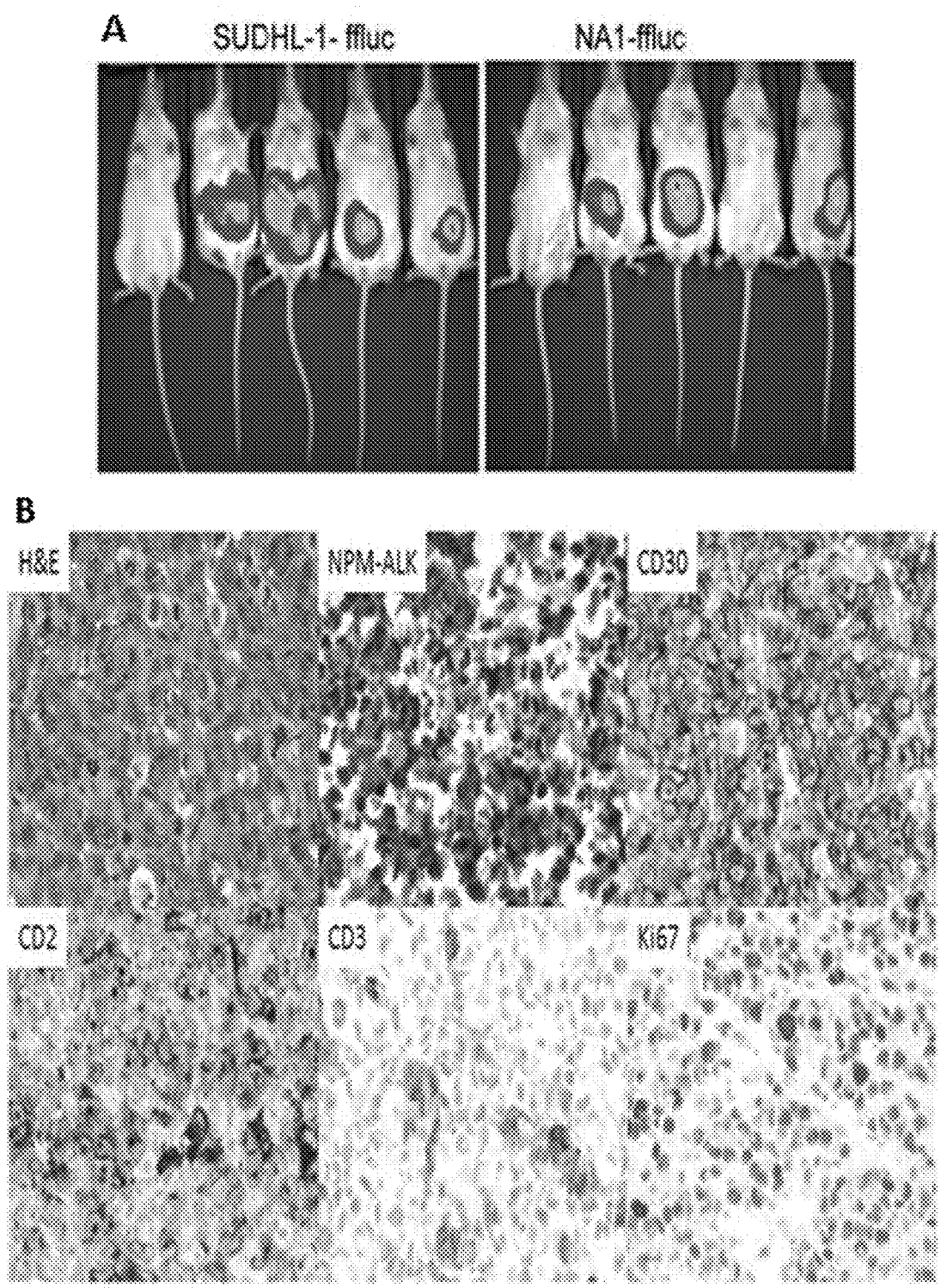
FIG. 4 A-B

|      | NA1     | NA2     | NA3     |
|------|---------|---------|---------|
| CD2  | + (dim) | + (dim) | + (dim) |
| CD3  | +/-     | +/-     | +/-     |
| CD4  | +       | +       | +/-     |
| CD5  | + (dim) | + (dim) | + (dim) |
| CD7  | + (dim) | + (dim) | + (dim) |
| CD8  | -       | -       | -       |
| CD19 | -       | -       | -       |
| CD20 | -       | -       | -       |

FIG.7

| Sample | MM1 | MM2 |
|---|---|---|
| NA1 | 230 and 239 bp peaks | 179 and 188/189 peaks |
| NA2 | 235 and 246 bp peaks | 195 bp peak |
| NA3 | 232 bp peak | 194 bp peak |

Flow cytometry analysis of tumor cells derived from the NPMALK-transformed CD4+ T cells (line NA1).

| Cell Type | Percentage | | |
|---|---|---|---|
| | Mouse #1 (5699) | Mouse #2 (5700) | Mouse 5702- NPM-ALK line #1 |
| CD3+CD5+ | 17 | 10 | 15 |
| CD3+CD4+ | 42 | 23 | 27 |
| CD3+CD7+ | 15 | 11 | 12 |
| CD3+CD5- | 28 | 20 | 17 |
| CD3+CD4- | 0 | 4 | 5 |
| CD3+CD7- | 28 | 18 | 20 |
| CD3-CD5+ | 20 | 11 | 20 |
| CD3-CD4+ | 41 | 18 | 23 |
| CD3-CD7+ | 4 | 5 | 5 |
| CD3-CD5- | 35 | 60 | 50 |
| CD3-CD4- | 16 | 55 | 45 |
| CD3-CD7- | 43 | 66 | 63 |

Negative for CD8, CD19, CD20, Ig kappa, Ig lambda in all three cases.

FIG. 11

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
aaggcgcatg tgaactcc                                                 18

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aaggcattct tcacctgctc                                               20

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
tctccagaac atcatccctg cctc                                          24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
tgggccatga ggtccaccac cctg                                          24
```

ANAPLASTIC LYMPHOMA KINASE (ALK) AS AN ONCOGENE CAPABLE OF TRANSFORMING NORMAL HUMAN CELLS

CROSS-REFERENCE TO RELATED APPLICATIONS

The present application claims priority under 35 U.S.C. §119(e) to U.S. Provisional Application No. 61/774,770, filed Mar. 8, 2013, which application is hereby incorporated by reference in its entirety herein.

STATEMENT REGARDING FEDERALLY SPONSORED RESEARCH OR DEVELOPMENT

This invention was made with government support under R01-CA89194, R01-CA96856, P01-A1080192, and R01-CA147795 awarded by the National Institutes of Health (NIH). The government has certain rights in the invention.

BACKGROUND OF THE INVENTION

Anaplastic large-cell lymphomas (ALCL) carrying anaplastic lymphoma kinase (ALK) comprise a distinct clinical-pathological entity (Li et al, 2007, Med Res Rev 28(3):372-412; Wasik et al., 2009, Semin Oncol 36(2 Suppl 1):527-35; Tabbó et al, 2012, Front Oncol 2:41). ALK+ALCL are derived from CD4+ T lymphocytes, typically occur in children and young adults, and involve soft tissues and other extranodal sites. As the name implies, they are comprised of large highly atypical cells with prominent nuclei and abundant cytoplasm and, hence, bear little resemblance to their normal CD4+ T-cell counterparts, either resting or activated. They also display a unique phenotype with the variable loss of CD3 and other T-cell markers and strong expression of CD30; a cell surface receptor from the TNF-R family.

While ALK is physiologically expressed only in a subset of immature neuronal cells (Li et al, 2007, Med Res Rev 28(3): 372-412), its aberrant expression has been identified in a subset of ALCL (Morris et al., 1994, Science 263(5151): 1281-1284; Shiota et al., 1994, Oncogene 9(6):1567-1574) and, subsequently, in a spectrum of histologically diverse malignancies including subsets of a large B-cell lymphoma, inflammatory myofibroblastic tumor, non-small cell lung carcinoma (Li et al, 2007, Med Res Rev 28(3):372-412; Wasik et al., 2009, Semin Oncol 36(2 Suppl 1):S27-35; Tabbó et al, 2012, Front Oncol 2:41) and several other types of cancer. The aberrant expression of ALK typically results in these malignancies from chromosomal translocations involving the ALK gene and various partner genes with the nucleophosmin (NPM) gene being by far the most frequent partner in ALK+ ALCL (Li et al, 2007, Med Res Rev 28(3):372-412) and EML4 in lung carcinoma (Soda et al., 2007, Nature 448:561-566). The NPM-ALK, EML4-ALK and other chimeric proteins are constitutively activated through autophosphorylation (Morris et al., 1994, Science 263(5151):1281-1284; Shiota et al., 1994, Oncogene 9(6):1567-1574) and highly oncogenic as documented mainly by using patient-derived cell lines and transgenic mouse models (Fujimoto et al., 1996, Proc Natl Acad Sci USA 93(9):4181-4186; Kuefer et al., 1997, Blood 90(8):2901-2910; Chiarle et al, 2003, Blood 101(5):1919-1927; Turner et al., 2006, Anticancer Res 26(5A):3275-3279; Giuriato et al., 2010, Blood 115(20): 4061-4070). NPM-ALK acts by activating a number of signal transduction pathways such as STAT3 (Zhang et al., 2002, J Immunol 168(1):466-474; Zamo et al., 2002, Oncogene 21(7):1038-1047) and mTORC1 including its down-stream target S6RP (Marzec et al., 2007, Oncogene 26(38):5606-5614). The chronic activity of these signaling pathways leads to the persistent modulation of a number of genes and results in sustained cell proliferation, resistance to cell death, and other oncogenic properties. NPM-ALK is capable of fostering evasion of the anti-tumor immune response by inducing expression of potent immunosuppressive proteins: the cytokine IL-10 and the cell membrane bound ligand PD-L1/CD274 (Marzec et al., 2008, Proc Natl Acad Sci USA 105(52): 20852-20857; Kasprzycka et al., 2006, Natl Acad Sci USA 103(26):9964-9969).

Cellular transformation by NPM-ALK has been demonstrated in immortalized rodent fibroblasts (Bai, R Y. et al. (1998) Mol Cell Biol. 18:6951-6961), and confirmed in studies which have shown that ALK protects Ba/F3 and PC12 cells from interleukin-3 or growth factor withdrawal (Stoica, G E., et al. (2001) J Biol. Chem. 276:16772-16779 and (Bai R Y., et al. (1998) Mol Cell Biol. 18:6951-6961). Transfer of NPM-ALK transduced bone-marrow cells into irradiated host recipient mice resulted in the generation in vivo of large cell B-cell lymphomas (Kuefer, M U. et al. (1997) Blood. 90:2901-2910). The later, even more refined studies using T-cell specific promoters resulted in the development of T-cell malignancies in the host mice (Chiarle et al. (2003) Blood 101:1919-1827). However, these tumors comprise of immature rather than mature T lymphocytes and lack key morphologic, phenotypic and other characteristics of human, patient-derived ALCL.

In the past few years, the molecular mechanisms of ALK-mediated cellular transformation have also been partially elucidated (Duyster, J. et al. (2001) Oncogene. 20:5623-5637). It has been shown that the ALK portion of the fusion protein, corresponding to the cytoplasmic tail of the ALK receptor and containing the catalytic domain, is absolutely required for transformation (Bai, R. Y. et al. (1998) Mol Cell Biol. 18:6951-6961), whereas all the N-terminal regions of the ALK chimeras function as dimerization domains (Bischof, D. et al. (1997) Mol Cell Biol. 17:2312-2325) and (Duyster, J. et al. (2001) Oncogene. 20:5623-5637). As a result of spontaneous dimerization, ALK undergoes autophosphorylation and becomes catalytically active. Constitutively active ALK fusion proteins can bind multiple adaptor proteins and activate a series of pathways involved in cell proliferation, transformation and survival. These include the PLC-Shc PI3-K/Akt and the Jak3-Stat3 pathways (Bai, R Y. et al. (1998) Mol Cell Biol. 18:6951-6961; Bai R Y., et al. (2000) Blood. 96:4319-4327 and Zamo, A. et al. (2002) Oncogene. 21:1038-1047).

Given limitations of the existing mouse models and cell lines derived from patient tumors, there is a clear need to develop new models of ALK-driven malignancies. In addition, there are no good models to transform normal human cells including T lymphocytes and bronchial epithelial cells, ALCL and lung carcinoma are derived from, respectively. Thus, there is a need in the art for a model of transformation by ALK chimeras in primary normal cells. The present invention satisfies this need in the art.

BRIEF SUMMARY OF THE INVENTION

The present invention provides compositions and methods for transforming primary mammalian cells, particularly human cells, using an oncogenic form of anaplastic lymphoma kinase (ALK) wherein the transformed cells display features of that of a corresponding tumor cell isolated from a cancer patient. The invention also provides a method for immortalizing normal CD4+ T lymphocytes with a lymphoma-characteristic form of ALK such as NPM-ALK.

The invention includes a composition comprising an isolated transformed mammalian cell, wherein the transformed cell is genetically modified to express an oncogenic ALK, and wherein the transformed cell exhibits one or more features of that of a corresponding tumor cell isolated from a cancer subject.

The invention further includes a method of immortalizing a primary normal mammalian cell. The method comprises genetically modifying the primary normal mammalian cell with an oncogenic ALK, wherein the immortalized cell exhibits a one or more features of that of a corresponding tumor cell isolated from a cancer subject.

The invention also includes a method for screening a test compound for antitumor activity. The method comprises contacting a transformed mammalian cell with a test compound, wherein the cell is genetically modified to express an oncogenic ALK, further wherein the cell exhibits a morphology of that of a corresponding cell isolated from a cancer subject. The method further comprises monitoring the antitumor activity of the test compound, wherein modulation of the morphology of the transformed cell after contact with the test compound is indicative of a compound having antitumor activity in comparison to the morphology of the transformed cell prior to contact with the test compound.

In certain embodiments, the composition comprises a transformed cell wherein the oncogenic ALK is selected from the group consisting of NPM-ALK, EML4-ALK, RANBP-ALK, TPM3-ALK, TFG-ALK, KIF5B-ALK, ATIC-ALK, CLTC-ALK and other ALK translocation variants as well as mutants such as R1275Q and F117L, and the like. In other embodiments, the composition comprises a transformed cell, wherein the cell is a T cell. In yet other embodiments, the composition further comprises a transformed cell wherein the cell exhibits one or more features of that of a corresponding tumor cell isolated from a cancer subject having anaplastic large-cell lymphoma. In yet other embodiments, the transformed cell exhibits one or more of perpetual cell growth, characteristic cell morphology, activation of the key signal transduction pathways and expression of CD30, IL-10 and PD-L1/CD274. In yet other embodiments, the mammalian cell is a human cell and the subject is a human.

In certain embodiments, prior to genetically modifying the primary normal mammalian cell, the cell is cultured in the presence of a composition comprising a first agent that is capable of providing a primary activation signal to a T cell and a second agent that is capable of activating a co-stimulatory molecule on a T cell. In other embodiments, the first agent is an anti-CD3 antibody and the second agent is an anti-CD28 antibody. In yet other embodiments, the cell is genetically modified using a lentivirus expressing the oncogenic ALK. In yet other embodiments, the cell exhibits one or more features of that of a corresponding tumor cell isolated from a cancer subject having anaplastic large-cell lymphoma morphology. In yet other embodiments, the immortalized cell is isolated. In yet other embodiments, the isolated immortalized cell can be grown in cell culture.

In certain embodiments, the method for screening a test compound for antitumor activity enables the identification of such a compound of interest.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A through 1F, is a series of images demonstrating NPM-ALK-induced malignant transformation of normal human CD4+ T lymphocytes. FIG. 1A depicts cell growth curves of NPM-ALK-expressing CD4+ T cells. Purified CD4+ T cells were stimulated with bead-immobilized CD3 and CD28 antibodies (ab) and either transduced with wild-type NPM-ALK (NA1) or enzymatically inactive NPM-ALK mutant (KD) or left untransfected. The cells were counted at the depicted days using a cell counter. FIG. 1B depicts cell growth curves of NPM-ALK-transfected CD4+ T cells (NA1, NA2, NA3) from three separate, consecutive experiments. FIG. 1C depicts activation of ALK, STAT3, and mTORC1 pathway as determined by phosphorylation status of the listed proteins. Expression of total NPM-ALK and β-actin (ACTB) served as controls. ALK+ALCL-derived cell line SUDHL-1, ALK-ALCL cell line 2B, and normal unstimulated CD4+ T cells were used as additional positive and negative controls. FIG. 1D depicts cell volume of NPM-ALK-transfected and untransfected CD4+ T cells as determined by cell counter counter analysis (Beckman Coulter, Brea, Calif.). ALK+ALCL-derived cell line SUDHL-1 served as a positive control. FIG. 1E depicts migration of NPM-ALK-transfected cells determined using a Transwell culture system. Cells transfected with the enzymatically inactive NPM-ALK (KD) and untransfected cells (Ctrl) served as controls. $P=0.01$ for NA1 and $P=0.04$ for NA3 versus combined KD and Ctrl. FIG. 1F depicts colony formation by the NPM-ALK-transfected NA1, NA 2, NA3 and control ALK+ALCL-derived SUDHL-1 cells.

FIGS. 2A through 2E, is a series of images depicting morphologic and immunophenotypic features of NPM-ALK-transformed CD4+ T cells. FIG. 2A shows H&E stain and immunohistochemical analysis for the depicted proteins of NA1 cells. Main image: 200× magnification, inset: 400×. FIG. 2B shows a multiparameter flow cytometry analysis of NA1 cells for expression of T-cell markers CD2 and CD3 (left panel) and CD4 and CD25 (right panel). FIG. 2C shows a flow cytometry analysis of the NA1 and NA2 for CD30 expression. ALK+ALCL-derived SUDHL-1 and mantle cell lymphoma derived Jeko cell line served as a positive and negative control, respectively. FIG. 2D shows the expression of IL-10 mRNA determined by RT-PCR in NA1 and NA2 cells, with CD3 and CD28-stimulated, NPM-ALK-untransfecte CD4+ T cells (Ctrl) serving as negative control. $P=0.01$ for the experimental versus control cells. FIG. 2E shows the expression of the immunosuppressive PDL-1/CD274 protein by NA1, and NA2, and control SUDHL-1 cells. Original magnification: ×200; ×400 (insets).

FIGS. 3A through 3I, is a series of images demonstrating NPM-ALK-dependence of the transformed CD4+ T cells. Suppressive effect of ALK inhibitor (CEP-28122, 100 nM) on (FIG. 3A) phosphorylation of the depicted cell signaling proteins in NA1, NA2 and control SUDHL-1 cells, (FIG. 3B) expression of CD30 (with CD30+ ALK-T-cell line 2A serving as a negative control, (FIG. 3C) synthesis of IL-10, and (FIG. 3D) expression of PDL-1. FIG. 3E depicts dose-dependent inhibition of cell growth by CEP-28122 ALK inhibitor. ALK-T-cell lines MyLa2059 and MyLa3675 served as negative controls. Depletion of NPM-ALK mediated by ALK siRNA (FIG. 3F; left panel) and its effect on phosphorylation of the depicted signaling proteins (FIG. 3F; right panel), expression of IL-10 (FIG. 3G) and PDL-1 (FIG. 3H), and cell growth (FIG. 3I). Non-specific (NS) siRNA was used as a negative control (FIGS. 3F-3I).

FIGS. 4A through 4C, is a series of images showing growth of the transformed CD4+ T cells in vivo. FIG. 4A shows the ability of NPM-ALK-transfected CD4+ T lymphocytes to form tumors in immunodeficient mice. NA1 and control SUDHL-1 cells were transfected with a vector containing luciferase gene, injected intraperitoneally at $3 \times 10^6$ cells/mouse. The mice were examined for the presence of bioluminescence 5 weeks later. FIG. 4B shows representative 400× images of an H&E and immunohistochemical stains for expression of the depicted proteins by the tumor tissues. FIG. 4C shows flow cytometry-detected expression of T-cell markers CD5 and CD3 (left panel) and CD4 and CD3 (right panel) by the isolated tumor cells.

FIG. 7 is a chart showing the immunophenotype of cell lines derived from the NPM-ALK transfected CD4+ T cells.

FIG. 11 is an image showing the results of flow cytometry analysis of tumor cells derived from the NPM-ALK-transformed CD4+ T cells (line NA1).

FIGS. 12A and 12B, is a series of images depicting NPM-ALK-dependent survival of transduced CD4+ T cells. FIG. 12A shows the effect of 100 nmol/L ALK inhibitor CEP-28122 on cell-surface annexin V expression and propidium iodide (PI) incorporation in cell lines NA1, NA2, SUDHL-1 (positive control), and MyLA3675 (negative control), FIG. 12B shows the effect NPM-ALK and nonspecific (NS) control siRNA on NA1 cell staining for annexin V and PI; the western blots show the degree of NPM-ALK depletion, with β-actin (ACTB) serving as control.

DETAILED DESCRIPTION OF THE INVENTION

Figure 1:
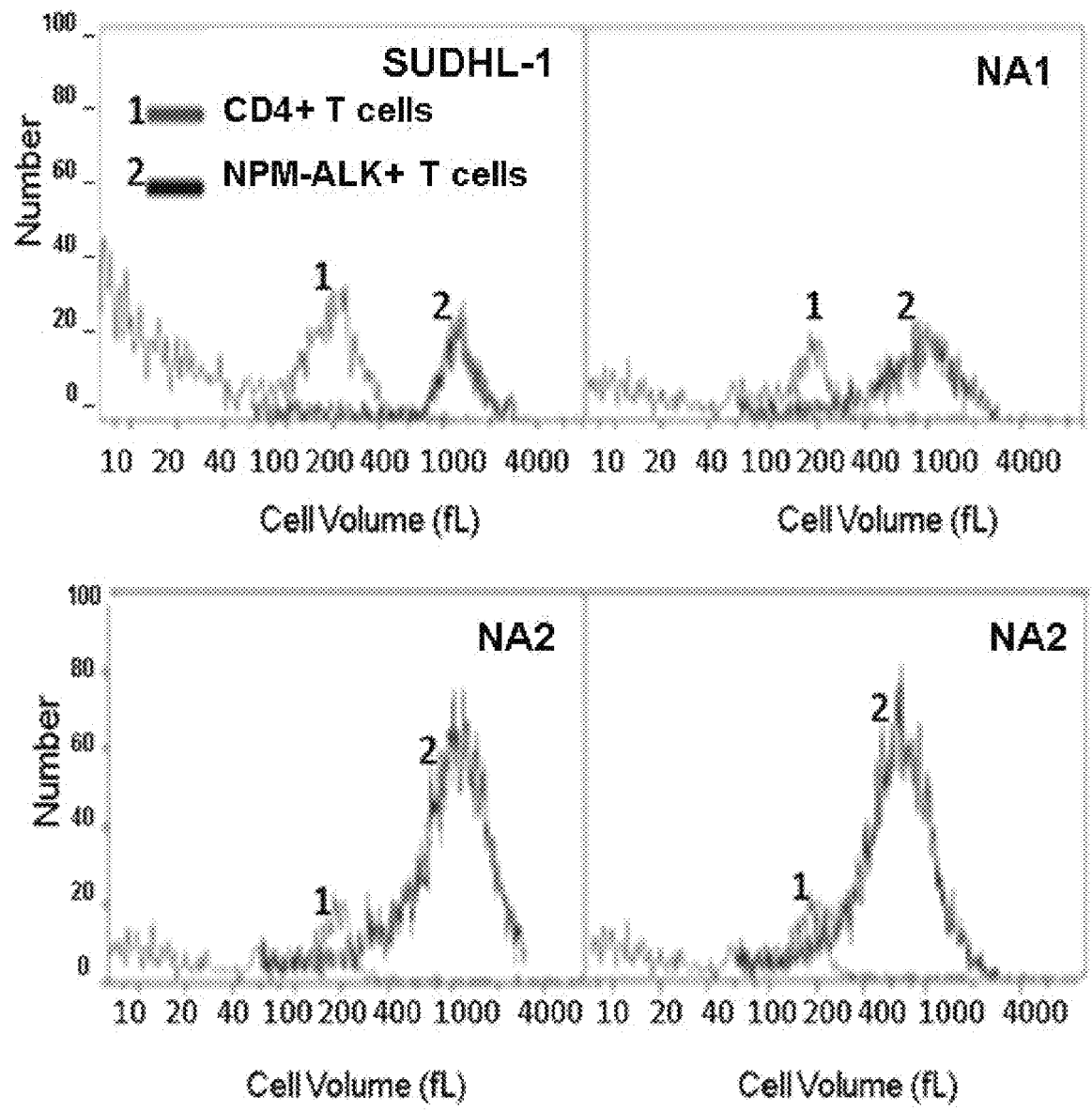
FIG. 1, comprising

It has been discovered that a primary normal human cell can be immortalized by introducing an oncogenic ALK into the cell, wherein the immortalized cell is morphologically and immunophenotypically indistinguishable from a corresponding malignant cell isolated from an ALK+ cancer patient. Accordingly, the invention provides an in vitro model of mechanisms of malignant transformation of normal human cells.

The invention is based partly on the successful in vitro transduction of normal human CD4+ T lymphocytes with the chimeric ALK gene that resulted in their malignant transformation. The transformed cells exhibit morphology and immunophenotype of that of a "naturally occurring" human malignancy derived from patients.

The invention allows for the generation of a malignant cell that recapitulates malignant cells found in a cancer patient. The cells of the invention are valuable in studying the early stages of oncogenesis and mechanisms of progression thereof. The cells of the invention offer an in vitro model for evaluating cancer features and its development as well as for screening of anti-cancer agents.

In one embodiment, the invention provides compositions and methods for transforming normal cells, such as CD4+ T lymphocytes, using a single oncogene (e.g., oncogenic ALK) wherein the transformed cells are morphologically and immunophenotypically indistinguishable from a malignant cell isolated from a cancer patient. In one embodiment, because the cells of the invention are immortalized due only to the expression of an oncogenic kinase (e.g., oncogenic ALK), the activities of the oncogenic kinase can be evaluated separately from other confounding mechanisms of oncogenesis that are present when not starting from a primary normal cell.

The present invention relates to a normal primary cell transduced with an oncogenic ALK and methods for their production and use. In certain forms of the invention, a method of screening for, or otherwise identifying, drugs or agents that modulate oncogene-mediated neoplastic or hyperplastic transformation, or increase the sensitivity of the cells of the invention to the toxic effects of radiation or chemotherapy, are provided. Additionally, the cells of the invention may be used as a model to study conserved pathways that lead to oncogene-mediated cancer progression.

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

"Allogeneic" refers to a graft derived from a different animal of the same species.

"Alloantigen" is an antigen that differs from an antigen expressed by the recipient.

The term "ALK" includes the human ALK protein encoded by the ALK (Anaplastic Lymphoma Kinase) gene which in its native form is a membrane-spanning protein tyrosine kinase (PTK)/receptor.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies included in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded soley by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

The term "cancer" as used herein is defined as disease characterized by the rapid and uncontrolled growth of cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "DNA" as used herein is defined as deoxyribonucleic acid.

As used herein, an "effector cell" refers to a cell which mediates an immune response against an antigen. An example of an effector cell includes, but is not limited to a T cell and a B cell.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "epitope" as used herein is defined as a part of an antigen that is recognized by the immune system and that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "heterologous" as used herein is defined as DNA or RNA sequences or proteins that are derived from the different species.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity."

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein".

"Proliferation" is used herein to refer to the reproduction or multiplication of similar forms of entities, for example proliferation of a cell. That is, proliferation encompasses production of a greater number of cells, and can be measured by, among other things, simply counting the numbers of cells, measuring incorporation of $^3$H-thymidine into the cell, and the like.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are culture in vitro. In other embodiments, the cells are not cultured in vitro.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art in light of this disclosure and their knowledge of the art.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "treat," "treating," and "treatment," refer to therapeutic or preventative measures described herein. The methods of "treatment" employ administration to a subject, in need of such treatment, a composition of the present invention, for example, a subject having a disorder mediated by ALK or other oncoprotein or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "ALK-mediated disorder" refers to disease states and/or symptoms associated with ALK-mediated cancers or tumors. In general, the term "ALK-mediated disorder" refers to any disorder, the onset, progression or the persistence of the symptoms of which requires the participation of ALK. Exemplary ALK-mediated disorders include, but are not limited to, cancer.

As used herein, an "oncogenic protein" refers to a protein that causes cancer. In some instances, activation of an oncogenic protein increases the chance that a normal cell will develop into a tumor cell. Non-limiting examples of an oncogenic protein is the NPM/ALK tyrosine kinase or other forms of oncogenic ALK, other chimeric tyrosine kinases, other oncogenic kinase, and the like.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Xenogeneic" refers to a graft derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for transforming a primary normal human cell into an immortalized cell that exhibits a morphology and immunophenotype of a corresponding cell isolated from a cancer patient. In one embodiment, the primary normal human cell is genetically modified with an oncogenic kinase, such as ALK, to transform the primary cell into an immortalized cell. Non-limiting examples of an oncogenic ALK includes but are not limited to NPM-ALK, EML4-ALK, RANBP-ALK, TPM3-ALK, TFG-ALK, KIF5B-ALK, ATIC-ALK, CLTC-ALK and other ALK translocation variants as well as mutants such as R1275Q and F117L, and the like.

In one embodiment, transforming a primary normal human cell into an immortalized cell that exhibits a morphology and immunophenotype of a corresponding cell isolated from a cancer patient can be accomplished by genetically modifying the normal cell with an oncogenic kinase, such as ALK as well as genes, RNA, proteins and the like that are regulated by ALK.

In one embodiment, the invention provides compositions and methods for transforming normal T cells with a lentiviral vector expressing an oncogenic kinase, such as ALK. Preferably, the T cell is CD4+ and the oncogenic ALK is NPM-ALK, wherein the transformed cell becomes immortalized and exhibits a morphology and immunophenotype of that of a lymphoma. In one embodiment, the immortalized cell exhibits a morphology and immunophenotype of that of a patient-derived anaplastic large-cell lymphoma (ALCL).

Compositions

Anaplastic Large Cell Lymphomas (ALCLs) carry translocations in which the anaplastic lymphoma kinase (ALK) gene is juxtaposed to various genes, the most common of which is the NPM/B23 gene. ALK fusion proteins result in the constitutive activation of ALK tyrosine kinase, thereby enhancing proliferation and increasing cell survival. The present invention is based on the discovery that normal cells can be immortalized by introducing an oncogenic ALK into a normal cell. In some embodiments, the normal cell is a T cell. In some embodiments, the T cell is a CD4+ T cell.

In one embodiment, the present invention provides an in vitro cell model of carcinogenesis in which human normal cells are transduced with an oncogenic ALK (e.g., NPM-ALK). Accordingly, the present invention provides compositions and methods for expressing oncogenic ALK in a normal cell to generate a cell that truly recapitulates features of a malignancy associated with expression of oncogenic ALK. In one embodiment, the malignancy associated with expression of oncogenic ALK is ALK+ALCL, a malignancy of mature CD4+ T lymphocytes with highly distinct morphology and phenotype.

In one embodiment, the invention provides an in vitro model of malignancy in which normal cells are genetically modified to express oncogenic ALK, such as NPM-ALK. Accordingly, the in vitro model of the invention can be generated by transducing normal cells, such as CD4+ T lymphocytes, with a lentiviral vector expressing the oncogenic ALK.

The cells or cell lines of the invention that are genetically modified with an oncogenic ALK may be used for screening new therapeutic agents for inhibition of cellular proliferation in vitro. In addition, the growth of these cells can be assessed in vivo following transplant into animal models. Novel therapeutic agents can then be tested in animals bearing these tumor cells containing the oncogenic ALK or variants and translocations thereof.

Accordingly, the cells of the invention provide a means for testing new therapeutic regimens and for screening and identifying novel compounds for use in treating cancers, including but not limited to ALK+ALCL, ALK+ non-small cell carcinoma, ALK+ inflammatory myofibroblastic tumor and other malignancies expressing oncogenic form of ALK.

The cells of the invention also provide a research tool for studying the effects of early therapeutic intervention and the mechanisms of malignant cell transformation and tumor progression. This is because the cells of the invention become immortalized and exhibit a morphology and immunophenotype to that of a corresponding cancer cell isolated from a cancer patient. In addition, because these cells are immortalized due to the expression of an oncogenic kinase (e.g., oncogenic ALK), the activities of the oncogenic kinase can be evaluated separately from other confounding mechanisms of oncogenesis that are present in tumors derived from cancer patients, such as established cell lines. Therefore the cells of the invention provide insight in the early stages and other key aspects of human oncogenesis.

The cells of the invention provide proof that malignant transformation of normal human cells recapitulating the "natural" carcinogenesis can be reproducibly achieved experimentally. Thus, the cells of the invention permit, among other things, the study of early stages of carcinogenesis, in particular the initial oncogene-host cell interactions.

In one embodiment, the cells of the invention allow for testing new therapeutic regimens and for screening and identifying novel compounds for use in treating cancers.

Sources of T Lymphocytes and Other Cells

The present invention provides compositions and methods for transforming primary normal human cells. The invention is partly based on the discovery that the oncogenic tyrosine kinase NPM-ALK is capable of transforming in vitro normal human CD4+ T lymphocytes and conferring upon these cells morphologic and immunophenotypic features characteristic of the patient-derived ALK+ALCL cells and tissues. However, the invention should not be limited to only CD4+ T cells. Rather, the invention encompasses any normal cells capable of becoming transformed by an oncogenic form of ALK.

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3 and CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3 and CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time.

Following the isolation of the desired cells from a subject, the cells can be cultured as described elsewhere herein.

Activation and Expansion of Cells

In one embodiment, the cells of the invention are generated by transducing normal cells, preferably purified normal CD4+ T lymphocytes, with a lentiviral vector expressing oncogenic ALK after pre-activating the cells with anti-CD3 and CD28 antibodies to foster an effective transduction.

In one embodiment, prior to genetically modifying the primary normal human cell with an oncogenic ALK or an equivalent thereof, the cell is cultured in the presence of a composition comprising a first agent that is capable of providing a primary activation signal to a T cell and a second agent that is capable of activating a co-stimulatory molecule on a T cell or their functional equivalents in epithelial and other cell types.

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8): 3975-3977, 1998; Haanen et al., *J. Exp. Med.* 190(9):13191328, 1999; Garland et al., *J. Immunol. Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or aphereseed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Vectors

Following activation by stimulating CD3 and CD28 receptors on the T cell, the activated cell is genetically modified to express an oncogenic kinase, such as ALK. Accordingly, the invention includes vectors useful for transducing an oncogenic kinase, such as ALK, into a T cell.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding oncogenic ALK is typically achieved by operably linking a nucleic acid encoding the oncogenic ALK polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Screening Agents

The invention includes a cell-based screening method comprises: bringing test substances into contact with a cell comprising an oncogenic kinase, such as ALK, of the invention by mixing (i.e., addition) (contact step); analyzing whether the cell expressing an oncogenic ALK of the present invention exhibits morphological or phenotypical changes or not by the test substance(s), by comparison with the morphological or phenotypical of the cell present invention not brought into contact with the test substances (analysis step); and selecting a substance altering the morphological or phenotypical of the cell of the present invention (i.e., a therapeutic agent for cancer, particularly, a therapeutic agent for lymphoma or lung cancer).

The invention includes a cell-based screening method comprises: bringing test substances into contact with a cell comprising an oncogenic ALK of the invention by mixing (i.e., addition) (contact step); analyzing whether the activity of the oncogenic ALK of the present invention is inhibited or not by the test substance(s), by comparison with the activity of the oncogenic ALK of the present invention not brought into contact with the test substances (analysis step); and selecting a substance inhibiting the activity of the oncogenic ALK of the present invention (i.e., a therapeutic agent for cancer, particularly, a therapeutic agent for lymphoma or lung cancer).

The invention also includes an expression inhibition-based screening method comprises: bringing test substances into contact with a cell expressing an oncogenic ALK by mixing (i.e., addition) (contact step); analyzing whether the expression of the oncogenic ALK is inhibited or not by the test substance(s), by comparison with the expression of the oncogenic ALK not brought into contact with the test substances (analysis step); and selecting a substance inhibiting the expression of oncogenic ALK (i.e., a therapeutic agent for cancer, particularly, a therapeutic agent for lymphoma or lung cancer, that is shown to be positive for the polynucleotide of the present invention).

In one embodiment, the screening method of the present invention further comprises, in addition to analyzing whether the oncogenic ALK is inhibited or not and selecting a substance inhibiting the polypeptide of the present invention, the step of confirming that the selected test substance has a therapeutic activity against cancer (particularly, lymphoma or lung cancer). Examples of the step of confirming that the selected substance has a therapeutic activity against cancer include a step of practicing an evaluation method known in the art or a modified method thereof.

A growth-inhibiting effect or cell death-inducing effect on the cells of the invention by the test substance can be confirmed by adding the test substance selected by the screening method of the present invention to a culture medium of the cells of the invention and measuring a cell count or cell death rate after culture by a standard method. If the selected test substance exhibits the growth-inhibiting effect and/or cell death-inducing effect on the cells, this selected test substance is confirmed to have a therapeutic activity against cancer. The test substance may be added to the medium under conditions in which the test substance is added at the start of culture or during culture once or any number of times without limitations. A culture period in the presence of the test substance can be set appropriately and is 5 minutes to 2 weeks, preferably 1 hour to 72 hours. Any of a variety of cell measurement methods may be used, such as trypan blue staining, Sulforhodamine, MTT, intracellular ATP measurement, and thymidine uptake methods, and any of a variety of cell death measurement methods may be used, such as LDH release measurement, annexin V staining, and caspase activity measurement methods.

The inhibitory effect of the test substance on the growth of the transformed cells of the invention can be examined with anchorage-independent growth, one feature of cancer cells, as an index to thereby determine a therapeutic activity against cancer. The anchorage-independent growth refers to, in contrast to adherent normal cells that must adhere to the extracellular matrix (anchorage) for their survival and growth, the general essential property of cancer cells capable of growing even without such an anchorage. One of most reliable methods for examining the carcinogenesis of cells is to confirm that the cells can grow without an anchorage. Whether cells transformed from normal cells by gene expression exhibit an anchorage-independent growth ability can be examined to determine whether the gene is an oncogene. The transformed cells of the invention also acquire an anchorage-independent growth ability. Therefore, the therapeutic activity of the test substance against cancer that is shown to be positive can be examined with this property as an index. The anchorage-independent growth of the transformed cells of the invention can be achieved by a method for cell culture in a soft agar medium or a method for cell culture in a plate capable of cell-culturing spheroids (cell aggregates).

In one embodiment, the invention provides methods of screening for drugs or agents that modulate (e.g., enhance or suppress) oncogene-mediated neoplastic or hyperplastic transformation. In one embodiment, a method includes (a) contacting or otherwise exposing a cell of the invention (e.g., a normal cell genetically modified with an oncogenic ALK) to a test drug or agent; (b) determining if the test drug or agent modulates (e.g., enhances or suppresses) oncogene-mediated neoplastic or hyperplastic transformation; and (c) classifying the test drug or agent as an drug or agent that modulates oncogene-mediated neoplastic or hyperplastic transformation if the test drug or agent suppresses or enhances oncogene-mediated neoplastic or hyperplastic transformation.

In another embodiment, the invention provides methods of screening for drugs or agents that modulate the sensitivity of the cells of the invention to treatment with radiation or chemotherapy. In one embodiment, the method comprises (a) contacting or otherwise exposing a cell of the invention to a test drug or agent; (b) determining if the test drug or agent modulates (e.g., suppresses or enhances) sensitivity to radiation- or chemotherapy-induced programmed cell death; and (c) classifying the test drug or agent as an drug or agent that modulates sensitivity to radiation- or chemotherapy-induced programmed cell death if the test drug or agent suppresses or enhances sensitivity to radiation- or chemotherapy-induced programmed cell death.

In one embodiment, the test drug or agent may suppress, or otherwise alter, or enhance expression of oncogene RNA and/or the oncogenic protein product, or RNA or protein expression of other genes involved in the oncogenic transformation process. Additionally, the test drug or agent may inhibit or stimulate the activity of other molecules involved, directly or indirectly, in the neoplastic/hyperplastic transformation process, or in the sensitivity of transgenic cells to treatments with radiation or chemotherapy. A wide variety of drugs or agents may be tested in the screening methods of the present invention. For example, small molecule compounds similar to those identified in Peterson, R. T., et al., Proc. Natl. Acad. Sci. U.S.A, 97: 12965-12969, (2000) and Peterson, R. T., et al. Curr. Biol., 11: 1481-1491, (2001) or a panel of FDA approved chemicals may be assayed. Small molecule compounds are identified by screening large chemical libraries for the effects of compound addition to the water of developing fish. Additionally, proteins such as oligo- and polypeptides, may also act as test drugs or agents.

Further examples of such test drugs or agents include oligonucleotides or polynucleotides, such as, for example, antisense deoxyribonucleic acid (DNA), antisense ribonucleic acid (RNA), and small interfering RNAs. The antisense nucleotide sequences typically include a nucleotide sequence that is complementary to, or is otherwise able to hybridize with, a portion of the target nucleotide sequence, such as the target nucleotide sequences described herein and others described herein. The antisense nucleotide sequence may have a length of at least about 10 nucleotides, but may range in length from about 10 to about 1000 nucleotides, or may be the entire length of the gene target. The skilled artisan can select an appropriate target and an appropriate length of antisense nucleic acid in order to have the desired therapeutic effect by standard procedures known to the art, and as described, for example, in Methods in Enzymology, Antisense Technology, Parts A and B (Volumes 313 and 314) (M. Phillips, ed., Academic Press, 1999).

Examples of the test substances used in the screening method of the present invention can also include, but not particularly limited to, commercially available compounds (including peptides), a variety of compounds (including peptides) known in the art and registered in chemical files, compound groups obtained by a combinatorial chemistry technique (N. Terrett et al., Drug Discov. Today, 4 (1): 41, 1999), microorganism culture supernatants, plant- or marine organism-derived natural components, animal tissue extracts, double-stranded nucleic acids, antibodies or antibody fragments, and compounds (including peptides) chemically or biologically modified from compounds (including peptides) selected by the screening method of the present invention.

In various embodiments, in vitro assays can be carried out with cells that harbor the NPM-ALK gene and that are representative of the tumor cell type involved in a subject's disease, to determine if a compound has a desired effect upon such tumor cell types. In one embodiment, the cells are T or B cell lymphomas, anaplastic large cell lymphomas, or multiple myelomas.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

A Potent Oncogene NPM-ALK Mediates Malignant Transformation of Normal Human CD4+ T Lymphocytes The results presented herein show that in vitro transduction of normal human CD4+ T lymphocytes with NPM-ALK results in their malignant transformation. The transformed cells become immortalized and display morphology and immunophenotype of patient-derived anaplastic large-cell lymphomas (ALCL). These unique features including the perpetual cell growth, activation of the key signal transduction pathways and expression of CD30, IL-10 and PD-L1/CD274 are strictly dependent on NPM-ALK activity and expression. Implantation of the NPM-ALK-transformed CD4+ T lymphocytes into immunodeficient mice results in formation of tumors indistinguishable from patient ALCL. This study demonstrates that the early stages and other key aspects of human oncogenesis can be faithfully reproduced in vitro when potent oncogenic stimulus is used to transform the "natural" target cells. The study provides proof-of-principle evidence that malignant transformation of normal human cells recapitulating the "natural" carcinogenesis can be reproducibly achieved experimentally. This finding stresses the key role in carcinogenesis of potent oncogenes when they become expressed in the relevant target cells. The transformed cells of this kind permit the study of early stages of carcinogenesis, in particular the initial oncogene-host cell interactions. This experimental approach also fosters studies into the effects of early therapeutic intervention and the mechanisms of malignant progression.

The materials and methods employed in the experiments disclosed herein are now described.

Materials and Methods

Lentiviral Transduction of CD4+ T Lymphocytes

De-identified purified human CD4+ T cells were obtained from the Human Immunology Core of the University of Pennsylvania under an IRB approved protocol. CD4+ T cells were activated by co-culture with anti-CD3/28 Ab-coated beads at the cell:bead ratio of 1:3. The cells were transduced 24 hr later by being exposed to lentiviral vectors containing NPM-ALK (wild type or kinase-deficient K210R mutant), either alone or together with GFP as part of T2A fusion construct (REF 18768965). Fresh medium was added to the cells on day 3 and twice weekly thereafter. On day 5, the magnetic beads were removed. The transduction efficiency was determined by flow cytometry by examining expression of GFP or NPM-ALK, the latter accomplished using anti-ALK ab (J606, BD Biosciences, San Jose, Calif.) and a Cytofix/Cytoperm™ fixation and permeablization Kit (BD Biosciences, San Jose, Calif.).

Cell Lines

The standard cell lines used in this study have been described previously (Marzec et al., 2007, Oncogene 26(38): 5606-5614; Marzec et al., 2008, Proc Natl Acad Sci USA 105(52):20852-20857; Kasprzycka et al., 2006, Natl Acad Sci USA 103(26):9964-9969). In brief, SUDHL-1 and JB6 cell lines were developed from ALK+ALCL and 2A (Mac-2A) cell line from the primary cutaneous ALK-ALCL. MyLa2059 and MyLa3675 cell lines were derived from cutaneous T-cell lymphomas. Jeko cell line was established from a mantle B-cell lymphoma. HEK 293 cells have been derived from human embryonic kidney (purchased from ATCC, Manassas, Va.).

Western Blotting

These experiments were performed using antibodies against phosphorylated (p)-ALK, p-STAT3, p-S6RP, total S6RP (Cell Signaling Technology), total NPM-ALK (Pharmigen, San Diego, Calif.), and total STAT3 and actin (ACTB), both from Santa Cruz Biotechnology (Santa Cruz, Calif.), according to the standard protocols.

Cell Migration

The cells were incubated for 20 hr in the FBS-free RPMI medium, washed, re-suspended in quenching medium (5% BSA-RPMI). They were applied at concentration of $2 \times 10^6$/ml in 250 ul to the top chamber of the Transwell system (Chemicon International) and 400 ul of RPMI with FBS media were added to the lower chamber. The plates were covered and incubated for 24 hr at 37° C. in an atmosphere containing 5% $CO_2$. Cells that passed through the membrane were collected from the lower chamber and added to a 96-well plate. Lysis Buffer/Dye Solution containing the CyQUANT green dye was added to all samples for 15' at room temperature and the plate was examined with a fluorescence plate reader (Molecular Devices) using the 480/520 nm filter set.

Colony Formation

The cells were plated for 21 days in the semi-solid agar prepared according to the standard protocol. The number of growing colonies was counted using an inverted microscope.

Flow Cytometry

The cells were analyzed using FACSCalibur (BD Biosciences) and, for data analysis, *CellQuest Pro software version* 6.03 (BD Biosciences). For the standard cell-surface staining, 0.5–1.0×10$^6$ cells were incubated for 20 minutes at 4° C. with 10-20 ul of fluorescein isothiocyanate-conjugated (FITC), phycoerythrin-conjugated (PE), or allophycocyanin-conjugated (APC) standard anti-T- and B-cell antibodies, PD-L1 or isotype control antibody (Bio-Legend, San Diego, Calif.). The intracellular staining was performed by using commercially available fixation and permeabilization reagents (BD Biosciences or Life Technologies, Carlsbad, Calif.). In brief, 0.5–1.0×10$^6$ washed membrane-stained or unstained cells were fixed for 15 minutes at room temperature with 100 ul of Fix/Per-solution or Fixation medium. After washing the cells were re-suspended in 100 ul of PBS or Permeabilization medium, and incubated for 15 minutes at room temperature with 10-20 ul of PE-labeled ALK or isotype control antibody (BD Biosciences). After additional washing, cells were analyzed by flow cytometry (FACSCalibur; BD Biosciences). Data acquisition and analysis were performed using CellQuest Pro software version 6.03 (BD Biosciences).

Immunohistochemistry

The immunohistochemical stainings were performed on formalin-fixed, paraffin-embedded cell blocks or xenotransplant tumor tissues using standard methods. In brief, the slides were heat-treated for antigen retrieval in 10-mM citrate buffer and sections were incubated with the diluted primary antibodies to ALK, CD30, CD2, MUM1, Ki67 (all from Dako, Carpinteria, Calif.) and CD3 (Novocastra, Leica Microsystems, Wetzlar, Germany). For interpretation, the immunostained slides were evaluated by light microscopy.

Cytogenetics

A metaphase arresting agent, Colcemid solution was added to cell cultures for 2 hours. Cells were exposed to hypotonic solution for 40 minutes at 37° C., followed with three changes of 1:3 glacial acetic acid and methanol solution. Cell suspension was dropped onto water wet microscope slides. Dried slides were aged at 600° C. oven for 14 hours and stained with Wright's stain for G-banding. Metaphase spreads were analyzed under 100× magnification of the bright field microscope, images captured and karyotypes were prepared using Gene Vision (Applied Imaging Computer Karyotyping System, Santa Clara, Calif.).

T-Cell Receptor Gene Rearrangement

DNA was extracted from cultured cells using conventional column based methods (Qiagen, Valencia, Calif.). Two separate multiplex PCR amplifications were performed using primers to relatively well-conserved regions in the V and J gene segments of the T cell receptor gamma locus (TRGg). PCR products were separated by capillary electrophoresis using an ABI 3130×1 system (Life Technologies). Peak size and height were determined using GeneMapper v3.7 software (Life Technologies). PCR product sizes are expected to range between 200 bp and 250 bp for the TRGg V gene segments 1 to 8 primer mix, and 150 bp and 200 bp for the TRGg V gene segments 9 to 11 primer mix.

siRNA Assay

A mixture of four siRNAs specific for ALK or control siRNAs (all from Dharmacon; Thermo Fisher Scientific, Waltham, Mass.) was introduced into cells using Lipofectamine 2000 as described previously (Marzec et al., 2008, Proc Natl Acad Sci USA 105(52):20852-20857) for SUDHL-1 cells and Nucleofector T-solution (Amaxa; Lonza, Walkersville, Md.) for CD4+ T-cell derived NA1 cells.

IL-10 Assay

IL-10 expression was using a Human Cytokine 10-Plex Antibody Bead Kit (Life Technologies) as per manufacturer protocol. Sample acquisition employed a Luminex Flex-MAP-3D (Life Technologies), and analyses performed using xPONENT software (version 4.0). A nine-point standard curve at threefold dilutions was employed with the range defined by 80%-120% of expected/observed values. Samples were tested in duplicate and CV was <10%. The results are presented as the decrease in the ALK inhibitor (CEP-28122)-treated cells relative to untreated cells.

RT-qPCR

Total RNA was extracted (RNeasy kit; Qiagen) and reverse transcribed using High Capacity RNA-to-cDNA kit (ABI). Expression levels of NPM-ALK mRNA were quantified by using an ABI/PRISM 7700 sequence detection system with TaqMan Gene Expression Assay kits (NPM-ALK, Hs03024829; β-actin, Hs9999903) (Life Technologies) and SYBR Green assay (Life Technologies) using primers for IL-10 (5'-AAGGCGCATGTGAACTCC-3'; SEQ ID NO: 1 and 5'-AAGGCATTCTTCACCTGCTC-3'; SEQ ID NO: 2) and for GAPDH (5'-TCTCCAGAACATCATCCCTGCCTC-3'; SEQ ID NO: 3 and 5'-TGGGCCATGAGGTCCACCAC-CCTG-3'; SEQ ID NO: 4. All assays were performed in duplicate. The fold difference in RNA levels was calculated on the basis of the difference between $C_T$ values obtained for control and individual mRNA ($\Delta C_T$).

MTT Enzymatic Conversion Assay

The cells suspended at 2×10$^4$/well were incubated at 37° C. in microtiter plates for up to two days, then incubated with MTT (Promega Madison, N.J.) for 4 hours. Well contents were solubilized overnight in the medium containing 10% SDS and 0.01M HCL. Absorbance at 570 nm in each well was measured using a Titertek Multiskan reader (Thermo Fisher Scientific).

Bromodeoxyuridine Incorporation Assay

The assay was performed using a cell-proliferation enzyme linked immunosorbent assay (ELISA; Roche Diagnostics, Indianapolis, Ind.) according to the manufacturer's protocol. In brief, cells were cultured at a concentration of 2×10$^4$ cells per well for 44 hours and labeled with bromodeoxyuridine for 4 hours. After centrifugation, supernatant removal, and plate drying, the cells were fixed and the DNA was denatured using FixDenat reagent (Roche Diagnostics). The amount of incorporated bromodeoxyuridine was determined by incubation with a specific antibody conjugated with horseradish peroxidase, followed by colorimetric conversion of the substrate and absorbance evaluation in the ELISA plate reader.

TUNEL Assay for DNA Fragmentation

TUNEL assay was performed using an ApoAlert DNA fragmentation assay kit (BD Biosciences) according to the manufacturer's protocol. In brief, cells were cultured at 0.5× 10$^4$ cells per well for 48 hours and then were collected, washed, fixed, permeabilized with 70% ethanol, washed again, and incubated in terminal deoxynucleotidyl transferase incubation buffer for 1 hour at 37° C. The reaction was stopped by adding 20 mmol/L EDTA. The cells were washed twice, resuspended in 0.5 mL of propidium iodide-RNase-PBS, collected, and analyzed by flow cytometry using a FACSCalibur system (BD Biosciences); data acquisition and analysis were performed using Cell-Quest Pro software (BD Biosciences).

Annexin V Expression Assay

For annexin V expression assay, cells were treated with the ALK inhibitor CEP-28122 (100 nmol/L) for 48 hours or with ALK siRNA (100 pmol/L) for 72 hours. After treatment, cells were washed with PBS and stained with anti-annexin V antibody and propidium iodide for 10 minutes, according to the manufacturer's instructions (Roche Diagnostics). The stained cells were analyzed by flow cytometry using a FACSCalibur system (BD Biosciences); data acquisition and analysis were performed using Cell-Quest Pro software (BD Biosciences).

Mouse Xenograft Tumor Formation

For tumor growth studies, NOD/SCID/IL-2Rγc$^{null}$ (NSG, JAX stock #005557, Jackson Laboratory, Bar Harbor, Me.) mice were generated by the Stem Cell and Xenograft Core (University of Pennsylvania School of Medicine) using stock breeders obtained from the Jackson Laboratory. Mice were housed in sterile conditions using HEPA-filtered microisolators and fed with irradiated food and acidified water. All experiments were conducted using mice aged 8 weeks in accordance with a protocol reviewed and approved by the Institutional Animal Care and Use Committee. The NPM-ALK transformed CD4+ T-cell lines NA1 and ALK+ALCL-derived SUDHL-1 line were transduced to express luciferase. On day 0, individual mice were implanted with $3 \times 10^6$ cells in 100 ul PBS by intraperitoneal administration. Mice were monitored weekly for tumor growth by visual examination and, starting with the week 3, bioluminescence imaging, which was conducted on anesthetized mice using a Xenogen Spectrum system and Living Image v3.2 software. For imaging, 10 mg/kg D-luciferin (Caliper Life Sciences) re-suspended in sterile PBS at a concentration of 15 mg/ml was administered intraperitoneally. Mice were imaged 12 minutes post-luciferin injection and serial images were collected at various exposures. Data were analyzed with Living Image v3.2 software using images taken with identical settings for mice in each group at each time point. Imaging data were converted to photons/second/cm$^2$/steradian to normalize each image for exposure time, f-stop, binning and mouse size.

The results of the experiments presented in this Example are now described.

NPM-ALK Induces Malignant Transformation of Normal CD4+ T Lymphocytes

Given the highly oncogenic phenotype of NPM-ALK and the CD4+ T-cell derivation of ALK+ALCL (Li et al, 2007, Med Res Rev 28(3):372-412; Wasik et al., 2009, Semin Oncol 36(2 Suppl 1):S27-35; Tabbó et al, 2012, Front Oncol 2:41), experiments were designed to transduce purified normal CD4+ T lymphocytes with lentiviral vector expressing the kinase after pre-activating the cells with anti-CD3 and CD28 antibodies to foster an effective transduction. Separate pools of the pre-activated CD4+ T cells were transduced with either a NPM-ALK mutant devoid of enzymatic activity (NPM-ALK-KD) or left untransduced. As shown in FIG. 1A, transfection with the native NPM-ALK led to sustained growth of the target cells. Although they displayed somewhat higher transfection efficiency (FIG. 5), the cells expressing inactive NPM-ALK reached the growth plateau by the second week and began to decline shortly afterwards, similar to untransfected cells. The same pattern of cell growth was seen in three independent consecutive experiments where the CD4+ T cell transfection with wild-type NPM-ALK resulted in the establishment of cell lines designated NA1, NA2, and NA3. These cell lines display a steady growth rate (FIG. 1B) and remain in continuous culture for at least eight months while the control cell populations ceased to grow by the 3-4 week of culture (FIG. 6). The established cell lines exhibited sustained expression of NPM-ALK as well as phosphorylation of the kinase at the concentration similar (NA1) or visibly lower (NA2) then the control, ALK+ALCL-derived SUDHL-1 cells (FIG. 1C). They also exhibited phosphorylation of direct target of NPM-ALK STAT3 and of its indirect, mTORC1-dependent target S6RP. These cells were also observed to be very large matching the size of the SUDHL-1 cells and markedly exceeding the size of the control CD3 and CD28-stimulated CD4+ T cells (FIG. 1D). They migrated (FIG. 1E) and formed colonies (FIG. 1F) and, hence, exhibited additional features of transformed cells.

Characteristics of the NPM-ALK Transformed Cells

Figure 2:
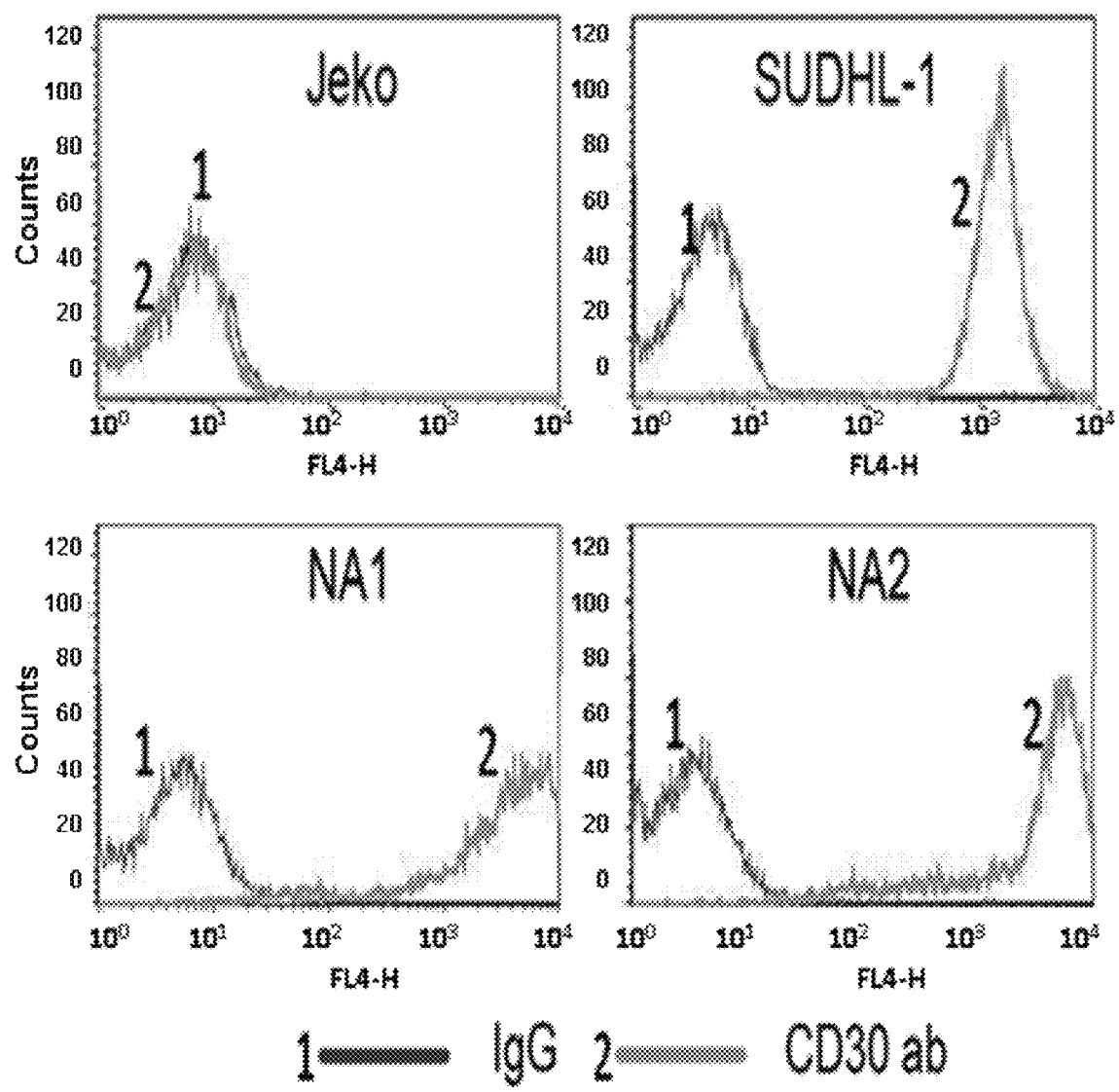
FIG. 2, comprising

Experiments were designed to examine the morphology and immunophenotype of the NPM-ALK-transformed CD4+ T cells. As shown in FIG. 2A, the cells displayed predominantly large nuclei with prominent nucleoli and moderate to abundant amount of the eosinophilic cytoplasm. In addition to expressing NPM-ALK, their subset weakly expressed T-cell related CD3 antigen and strongly expressed proliferation-related Ki67 antigen as determined by immunohistochemistry. Of note, the cells universally and strongly expressed CD30 and IRF4/MUM1 antigens. The marked loss of CD3 expression was confirmed by flow cytometry where diminished expression of CD5 and strong expression of CD4 and CD25 were also observed (FIG. 2B). The strong CD30 expression was also confirmed by this method (FIG. 2C). As summarized in FIG. 7, the cells further mimicked ALK+ ALCL cells by variably expressing T-cell markers: CD2 and CD7, among other features. Because ALK+ALCL cells universally express the immunosuppressive molecules IL-10$^{14}$ and PD-L1 (Marzec et al., 2008, Proc Natl Acad Sci USA 105(52):20852-20857), experiments were designed to examine the NPM-ALK-transformed CD4+ cells for the expression of these two immunosuppressive molecules. Indeed, both were expressed by the transformed cells (FIGS. 2D and 2E, respectively).

Figure 8:
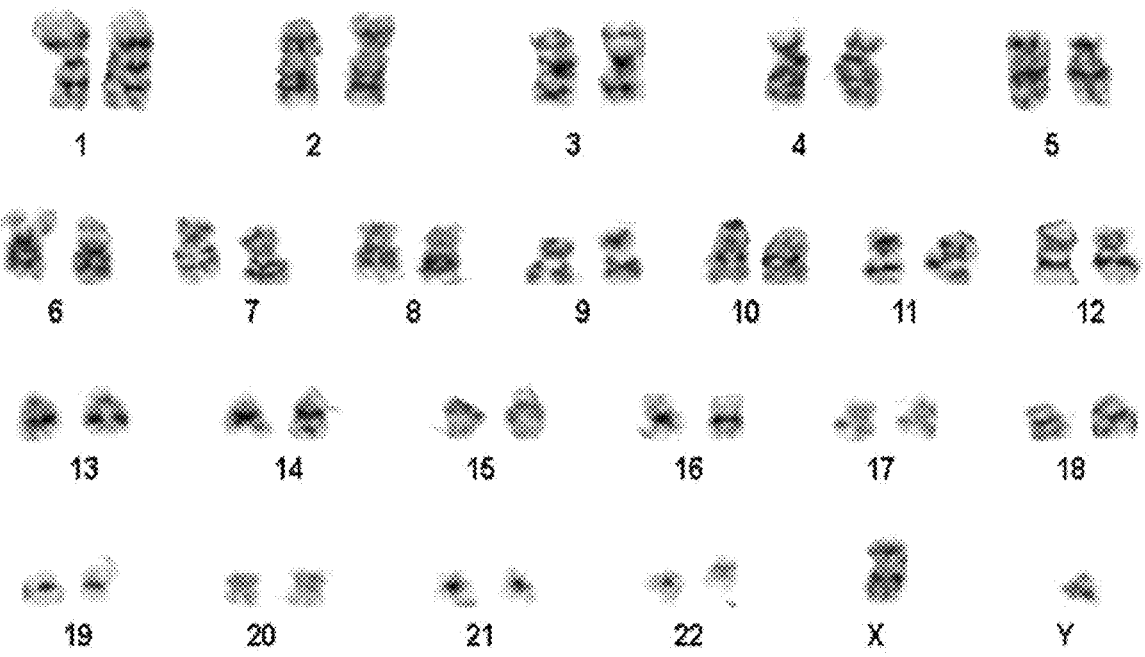
FIG. 8 is an image showing cytogenetic analysis of NA1 and NA2 cell lines derived from the NPM-ALK-transfected CD4+ T cells. Representative normal karyotypes of the NA1 (upper) and NA2 (lower) lines are shown.
Figure 8:
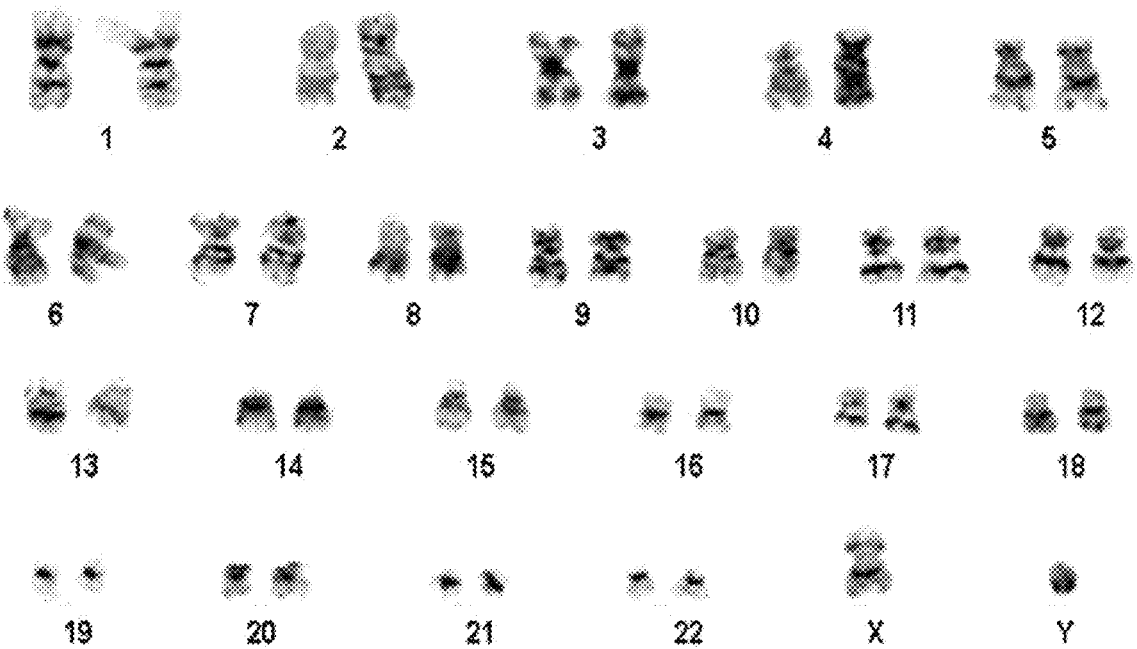

To further characterize the NPM-ALK-transformed CD4+ T cells, their karyotype and clonality were evaluated. Both NA1 and NA2 analyzed displayed essentially normal cytogenetics with only occasional random changes identified (FIG. 8). However, these two cell lines as well as NA3 showed two to four distinct peaks in the T-cell receptor gamma chain rearrangement PCR study that used two separate primer pairs (FIG. 9), indicating mono-to oligoclonal nature of the transformed CD4+ T lymphocytes.

Transformed Cells are Strictly NPM-ALK-Dependent

Figure 3:
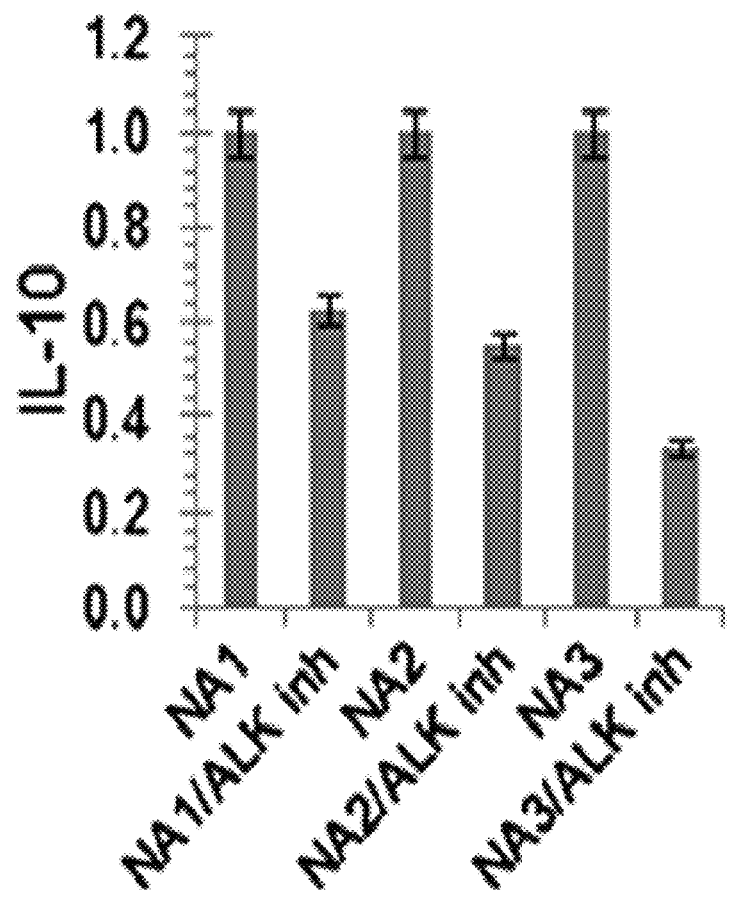
FIG. 3, comprising
Figure 3:
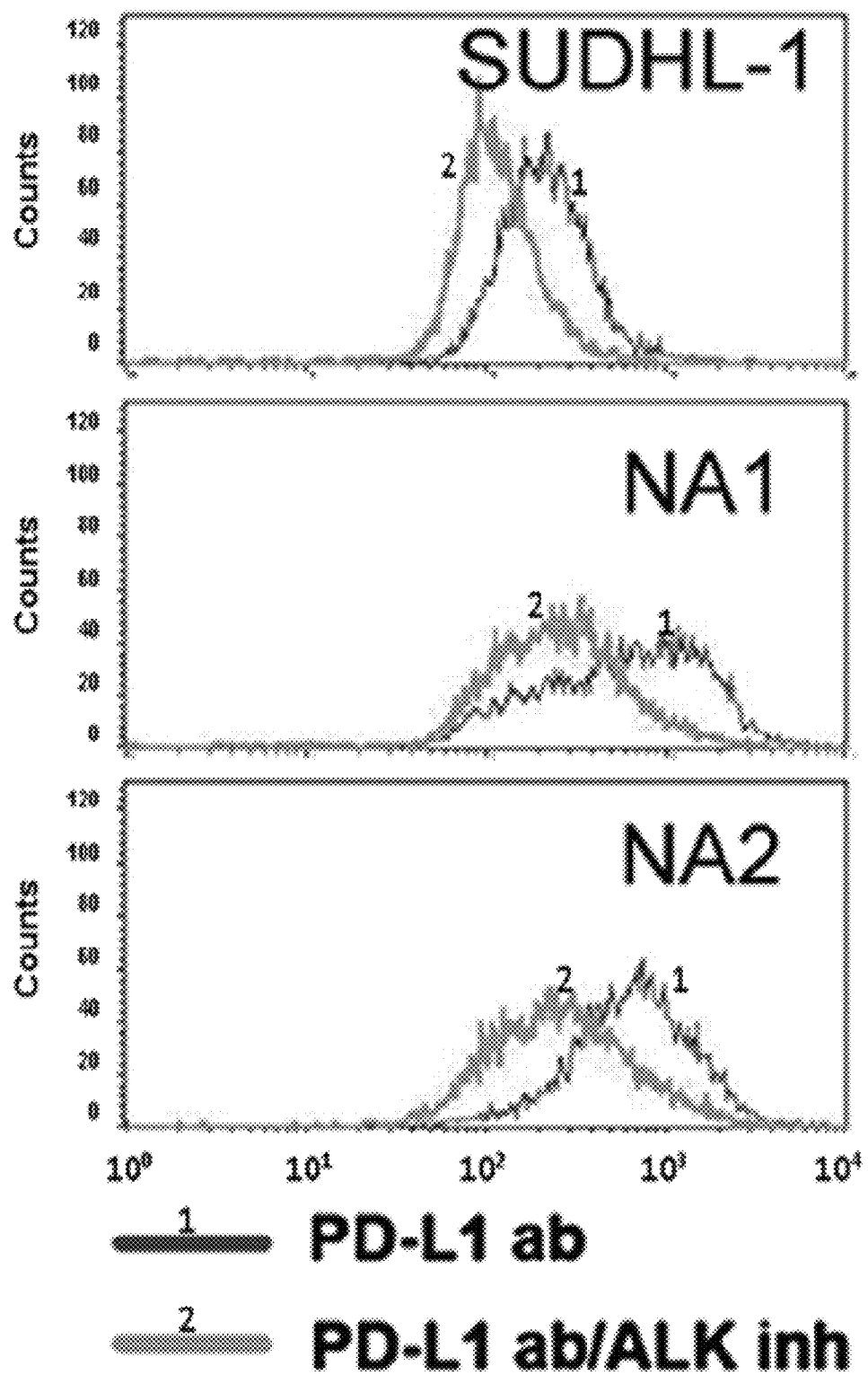
Figure 3:
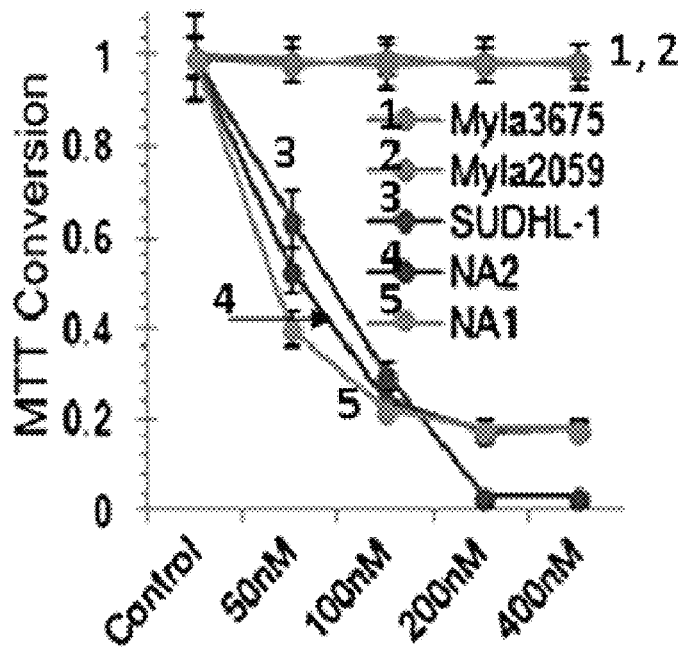
Figure 3:
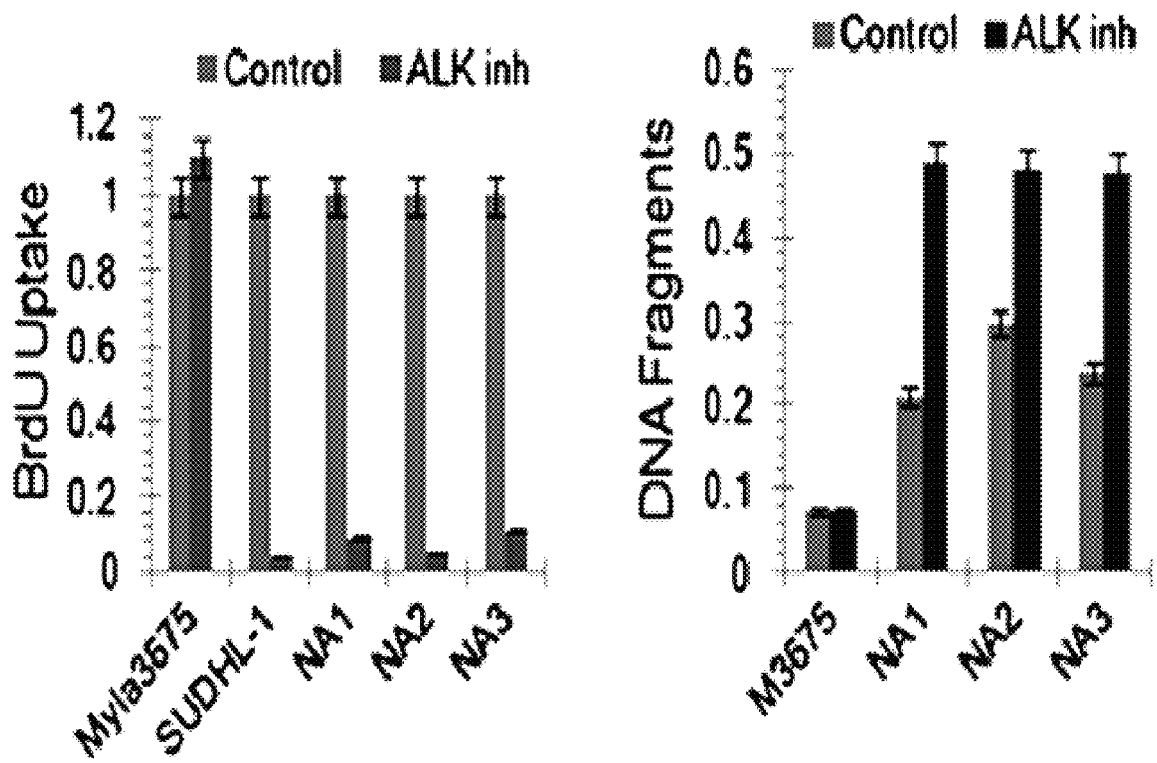
Figures 9, 10:
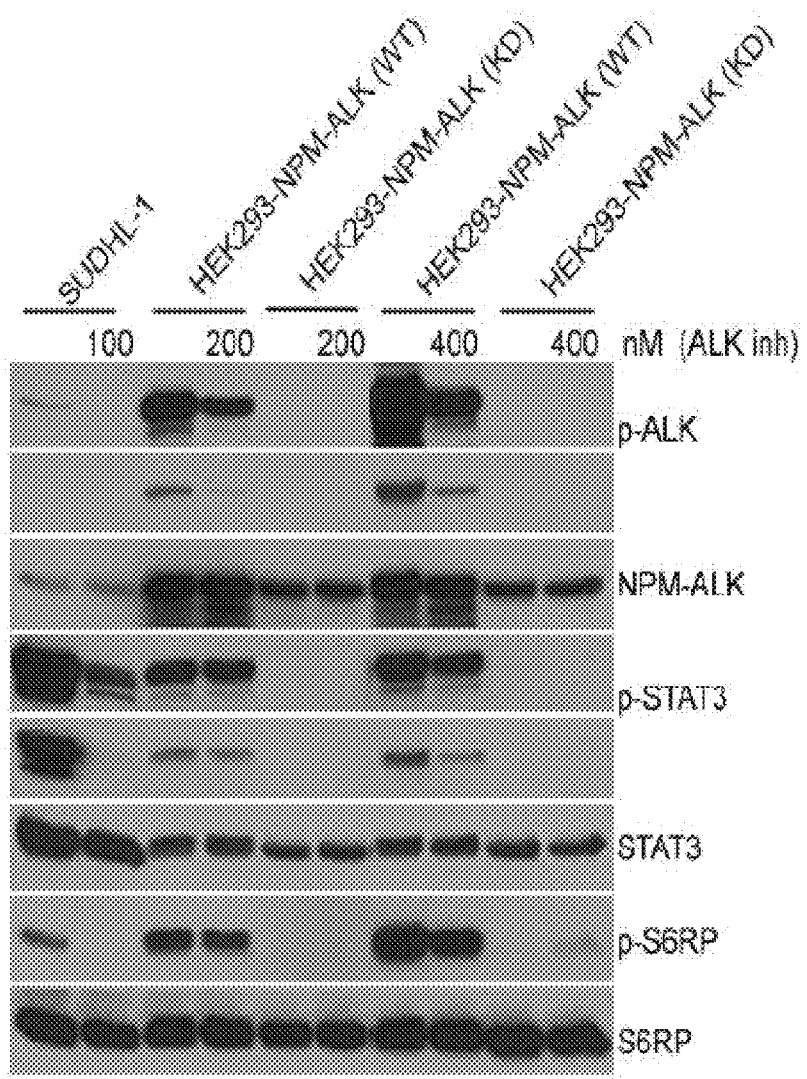
FIG. 9 is a chart showing T-cell receptor (TCR) gene rearrangement in NPM-ALK-transfected CD4+ T cells.
FIG. 10 is an image showing the effect of ALK inhibitor (ALK inh) CEP-28122 on activation of ALK and its targets. The cells were exposed to the inhibitor at the indicated doses and examined for the expression of the depicted phosphoproteins with the total proteins serving as controls.
Figure 12:
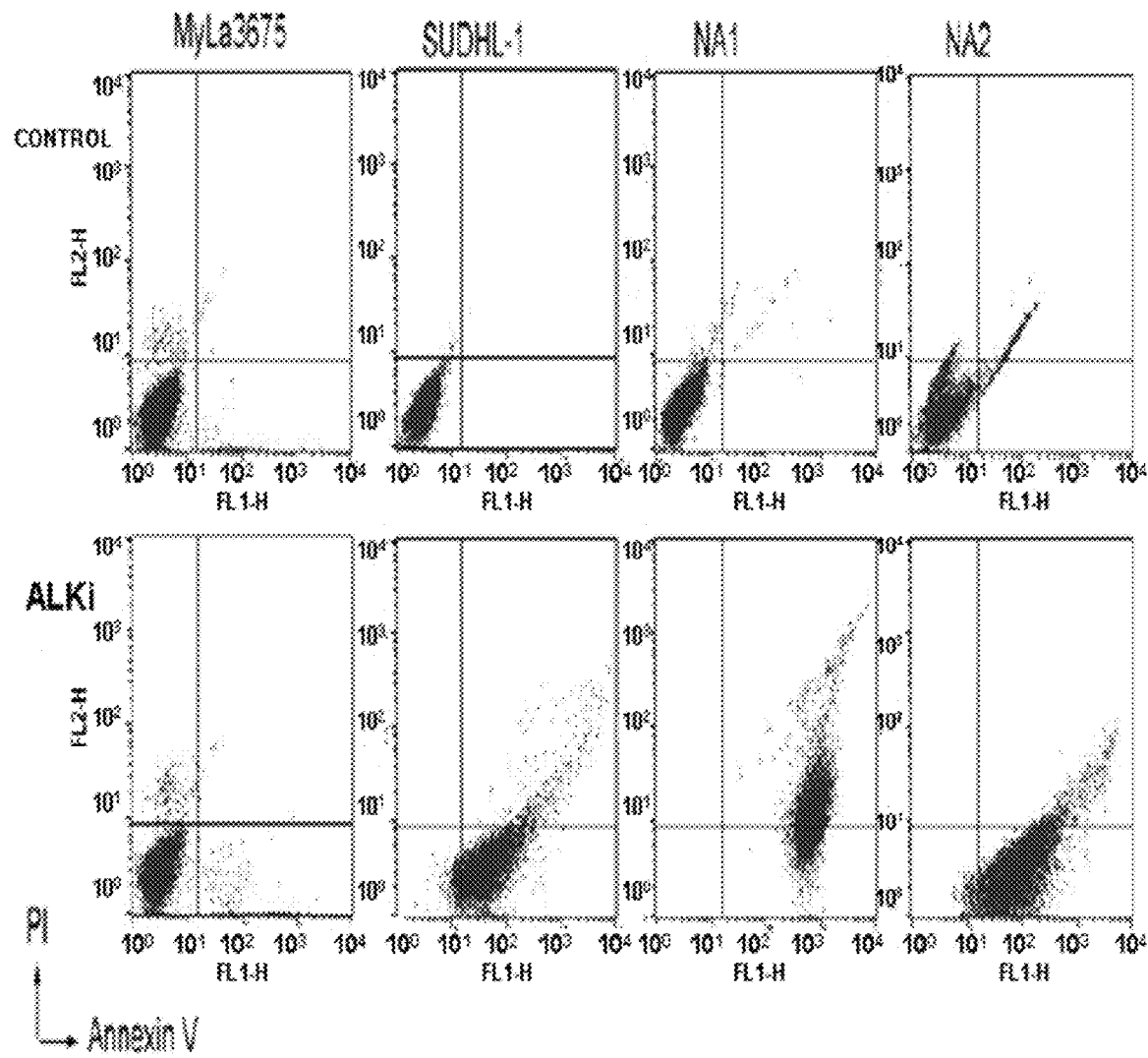
FIG. 12, comprising
Figure 12:
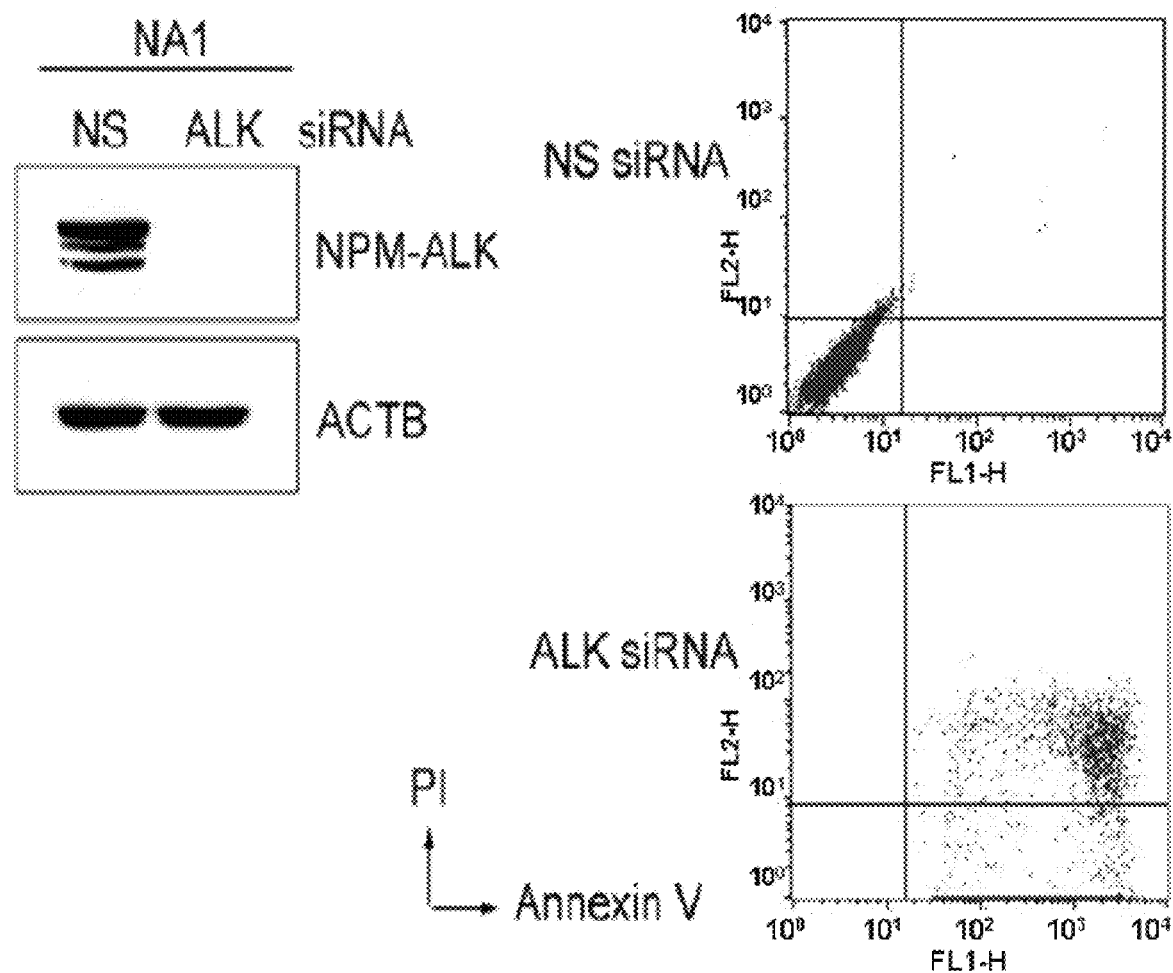

In the next series of experiments, the effects of suppression of NPM-ALK on the cells were evaluated. A highly selective ALK inhibitor was used (Cheng et al., 2012, Mol Cancer Ther 11(3):670-679) followed by ALK-targeting siRNA. Cell signaling is ALK-dependent in the transformed cells as documented by the ALK inhibitor-induced suppression of phosphorylation of the key proteins: ALK itself, STAT3, and S6RP (FIG. 3A). A similar result was obtained in the NPM-ALK-transfected epithelial HEK cells, although higher dose of the inhibitor had to be used to suppress ALK, STAT3, and S6RP phosphorylation due to high concentration of NPM-ALK expressed by these easily transfectable cells (FIG. 10). Furthermore, HEK cells transfected with the enzymatically inactive NPM-ALK-KD failed to phosphorylate ALK, STAT3, and S6RP, further supporting the key role of NPM-ALK in their activation. Because expression of CD30, the hallmark of ALK+ALCL, has been reported as being NPM-ALK-dependent (Hsu et al., 2006, Cancer Res 15(18):9002-9008), experiments were designed to examine whether this is the case in the NPM-ALK-transformed CD4+ T cells. Indeed, ALK inhibition diminished CD30 expression not only in the ALK+ALCL-derived cells but also in the transformed CD4+ T cells, while having no effect on CD30 expression in the cells from a different type T-cell lymphoma that is ALK negative (FIG. 3B). Similarly to CD30, expression of the immunosuppressive proteins IL-10 and PD-L1 is ALK-dependent in the NPM-ALK-transformed CD4+ T cells (FIGS. 3C and 3D, respectively). ALK is also critical for the transformed CD4+ T cells on the functional level, since ALK inhibition suppressed their growth (FIG. 3E and FIG. 12A). Depletion of NPM-ALK by siRNA yielded results similar to its inhibition including loss of ALK, STAT3, and S6RP phosphorylation (FIG. 3F), IL-10 (FIG. 3G) and PD-L1 expression (FIG. 3H), and impairment of cell growth (FIG. 3I and FIG. 12B).

In Vivo Tumor Formation

Figure 4:
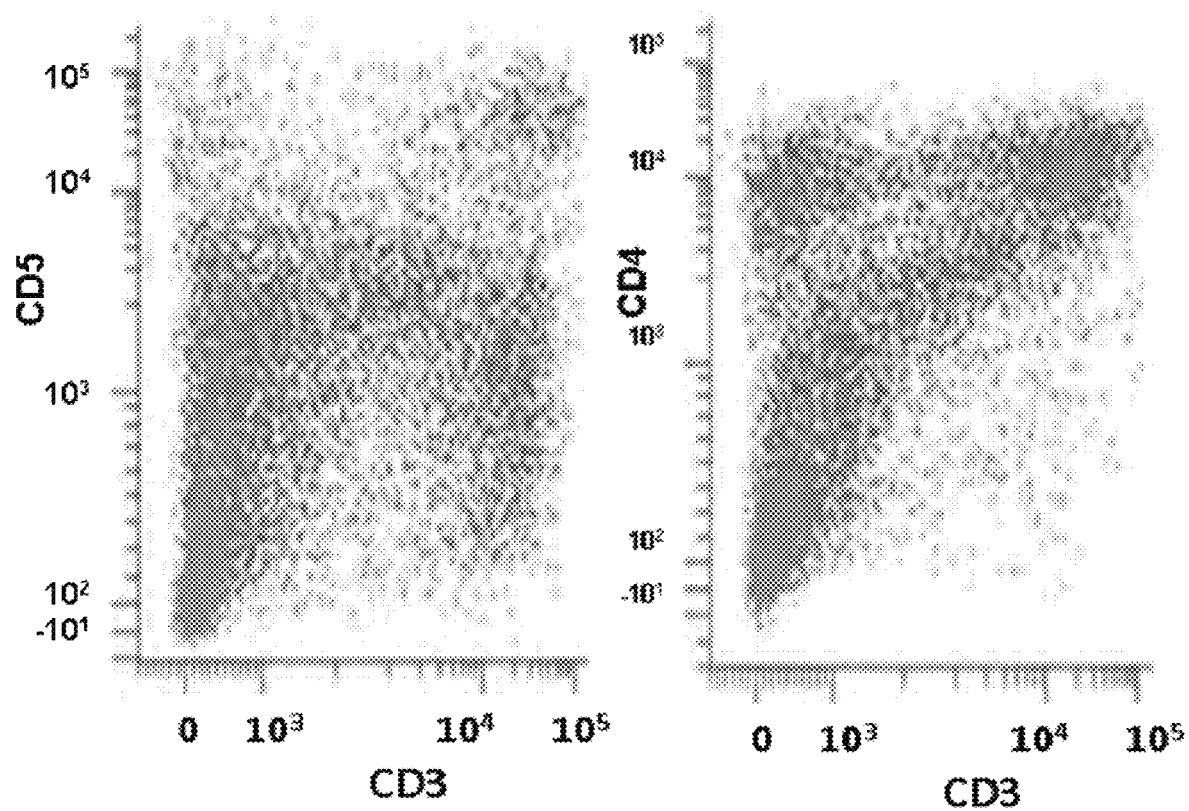
FIG. 4, comprising

As shown in FIG. 4, the NPM-ALK-transformed cells are capable of forming tumors in vivo as xenotransplants in the immunodeficient NSG mice. Within five weeks from injection, three out of five mice developed large tumors as compared to four out of five mice injected with ALK+ALCL cells (FIG. 4A). The tumors are indistinguishable from native ALK+ALCL as determined by anaplastic large cell morphology and the immunophenotype including expression of NPM-ALK, CD30, variable loss of T-cell antigens, and high proliferative rate (FIGS. 4B and 4C and FIG. 11). All the above findings indicate that NPM-ALK induces malignant transformation of normal human CD4+ T lymphocytes.

NPM-ALK Induces Malignant Transformation of Normal Human CD4+ T Lymphocytes

The understanding of carcinogenesis has been facilitated by development of various experimental models including tumor-derived cell lines and oncogene-expressing transgenic mice. However, these models have significant limitations. Only a handful of cell lines exist for any given malignancy and they originate almost exclusively from aggressive, clinically advanced tumors precluding studies of the early stages of carcinogenesis and the mechanisms of progression. Essentially all transgenic mouse models recapitulate only some features of the human malignancies; this certainly is the case in regard to the NPM-ALK transgenic mice. Efforts of several research groups using different gene promoters resulted in development of NPM-ALK-driven lymphomas but all these lymphomas are of either diverse B-cell or immature T-cell origin (Kuefer et al., 1997, Blood 90(8):2901-2910; Chiarle et al, 2003, Blood 101(5):1919-1927). None of the transgenic mouse models truly recapitulates features of ALK+ALCL, a malignancy of mature CD4+ T lymphocytes with highly distinct morphology and phenotype.

In vitro malignant transformation of normal human cells has been a goal of cancer research for quite some time. The efforts to recreate carcinogenesis in this manner were met with some success, most notably by immortalizing B lymphocytes using an oncogenic virus and epithelial cells using a combination of oncogenes. While normal B lymphocytes can routinely be immortalized by the Epstein-Barr virus (EBV) (Klein et al., 2010, Biochem. Biophys. Res. Commun 396(1): 67-73), the transformed cells resemble most closely lymphoproliferative disorders seen in transplant patients and other immunodeficient individuals rather than bona fide lymphomas occurring in the population at large. Furthermore, EBV genome contains almost 100 genes with expression of at least nine members from the EBNA and LMP gene families being seemingly critical to achieve the immortalization. Other investigations successfully transformed normal human fibroblasts and primary breast epithelial cells into neoplasms (Ince et al., 2007, Cancer Cell 12(2):160-170; Elenbaas et al., 2001, Genes Dev 15(1):50-65; Hahn et al., 1999, Nature 400(6743):464-468) using simultaneously three separate retroviral vectors containing and genes encoding hTERT unit of telomerase, H-ras oncogene, and simian virus SV40 early response region coding for large and small viral T antigens. Hence, three, if not four, distinct genes were required to accomplish the transformation. Perhaps more importantly, these gene combinations and specifically the SV40 T antigen(s) have not been unequivocally implicated in pathogenesis of the naturally occurring human malignancies.

In this context, it is remarkable that the results presented herein demonstrate the successful transformation of normal CD4+ T lymphocytes using a single oncogene NPM-ALK and that the transformed cells are morphologically and immunophenotypically virtually indistinguishable from the patient-derived ALK+ALCL. Previous studies have demonstrated that NPM-ALK tyrosine kinase is a very powerful oncogene capable of activating several key cell signaling pathways including STAT3 and mTORC1. (Li et al, 2007, Med Res Rev 28(3):372-412; Wasik et al., 2009, Semin Oncol 36(2 Suppl 1):S27-35; Tabbó et al, 2012, Front Oncol 2:41; Zhang et al., 2002, J Immunol 168(1):466-474; Marzec et al., 2007, Oncogene 26(38):5606-5614; Zamo et al., 2002, Oncogene 21(7):1038-1047). Activation of these multiple pathways modulates expression of a myriad of diverse genes which regulate the key oncogenic cell functions including the sustained cell growth and evasion of immune response. This pluripotency of ALK, a cell-surface receptor in its native form, is the most likely cause of its ability to transform the normal CD4+ T cells. In principle, other cell surface tyrosine kinase receptors such as members of the EGF-R family or even the IL-3R-mimicking cytoplasmic BCR-ABL, a very powerful oncogene in its own right sharing a number of characteristics with NPM-ALK (Shah et al., 2012, Blood 119(15):3374-3376), not to mention the other oncogenic forms of ALK including ELM4-ALK (Li et al, 2007, Med Res Rev 28(3):372-412; Wasik et al., 2009, Semin Oncol 36(2 Suppl 1):527-35; Tabbó et al, 2012, Front Oncol 2:41), should also be able to effectively transform in vitro the normal cells they target in vivo.

Figure 5:
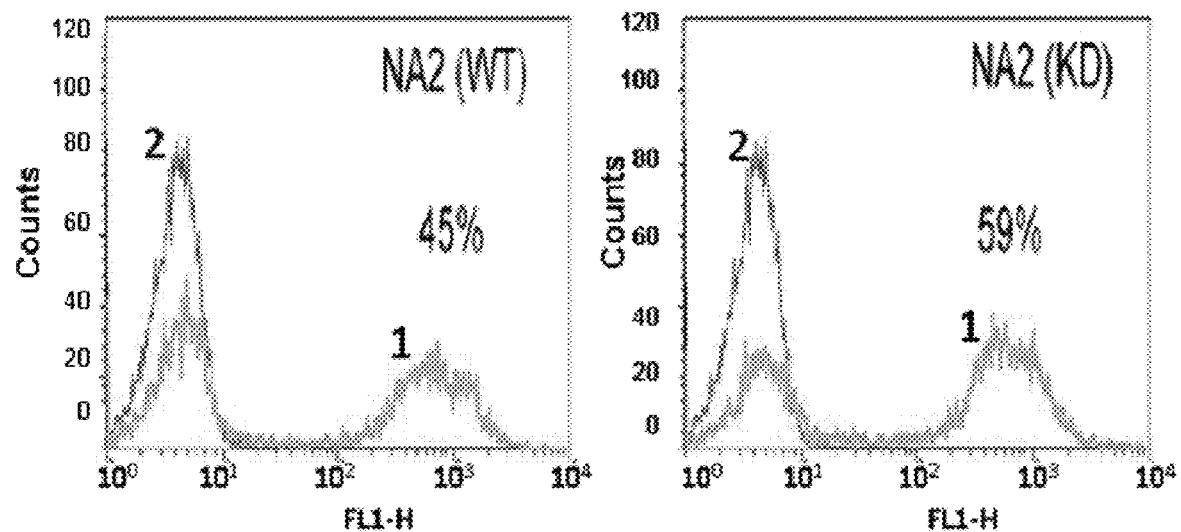
FIG. 5 is an image showing the transfection efficiency of the NPM-ALK WT and KD constructs. Normal CD4+ T cells prestimulated with CD3 and CD28 antibody-coated beads (ab/beads) were transfected with the NPM-ALK and stained with an anti-ALK ab (marked by "1") or IgG (marked by symbol "2") five days later. The data are representative of three independent experiments in which expression of NPM-ALK or GFP (for the NPM-ALK-GFP constructs) was measured.
Figure 6:
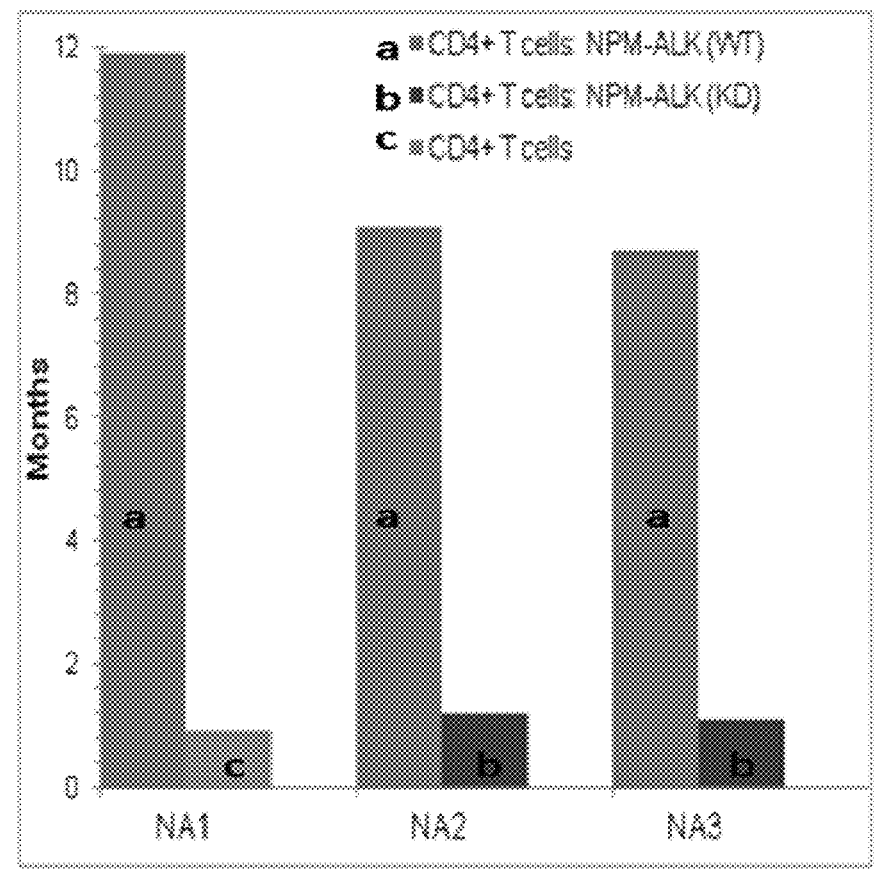
FIG. 6 is an image showing the growth time of CD4+ T lymphocytes transfected with NPM-ALK. Normal CD4+ T lymphocytes were transfected with NPM-ALK and remain in on-going culture for the indicated periods of time. The CD4+ T cells either non-transfected or transfected with the enzymatically inactive NPM-ALK-KD mutant served as controls.

It is interesting that the NPM-ALK immortalized cells are clonal, given the high transduction rate of CD4+ T cells (FIG. 5). Similar phenomenon has also been noted by others in the multigene, SV40 T antigen-based cell transformation system. (Ince et al., 2007, Cancer Cell 12(2):160-170). At least two scenarios may be considered to explain this phenomenon. First is that additional genetic changes are required to achieve the transformation. On one hand, the high success rate of immortalization achieved in several separate experiments, normal karyotype of the NPM-ALK transformed clones, and the young age of the ALK+ALCL patients argue to some degree against this option. The recent observation that highly malignant rhabdoid cancers in children display very few genetic changes with a loss of a single gene SMARCB1 being the sole common genomic lesion (Lee et al., 2012, J Clin Invest 122(8):2983-2988) supports this conclusion. In contrast, the ability of NPM-ALK to impair DNA repair resulting in increased mutation rate (Young et al., 2011, Am J Pathol 179(1):411-421), suggest that the secondary genetic changes may be required and can occur. The second scenario is that only a small subset of the CD4+ T lymphocytes undergoes the effective NPM-ALK-induced malignant transformation. CD4+ T cells are phenotypically and functionally quite diverse so it is possible that only their minor subset becomes transformed by NPM-ALK. Accordingly, a recent study indicates a resemblance of ALK+ALCL cells to the Th17 subset of the CD4+ T lymphocytes (Matsuyama et al., 2011, Blood 118(26):6881-6892). Furthermore, ALK+ALCL may contain a very minor stem cell population critical for their development, as postulated recently for MALT B-cell lymphoma (Vicente-Dueñas et al., 2012, Proc Natl Acad Sci USA 109 (26):10534-10539).

In summary, the results presented herein demonstrate that the oncogenic tyrosine kinase NPM-ALK is capable of transforming in vitro normal CD4+ T cells and conferring upon these cells morphologic and immunophenotypic features characteristic of the patient-derived ALK+ALCL cells and tissues. This study documents effective malignant transformation of normal human cells by a potent oncogene with the product cells faithfully recapitulating malignant cells encountered in ALK+ALCL patients. The cells generated by this manner should prove invaluable in studying the early stages of oncogenesis and, possibly, the mechanisms of progression. They should also be useful in evaluating anti-cancer agents including ALK inhibitors that have already shown substantial efficacy in ALK-driven malignancies (Kwak et al., 2010, N Engl J Med 363:1693-1703; Gambacorti-Passerini et al., 2011, N Engl J Med 364(8):775-776).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of immortalizing an isolated primary normal human cell, the method comprising genetically modifying the isolated primary normal human cell with an oncogenic anaplastic lymphoma kinase (ALK), wherein the immortalized isolated primary normal human cell is cultured in vitro and exhibits a one or more features of that of a corresponding tumor cell isolated from a human cancer, and wherein prior to genetically modifying the isolated primary normal human cell, the cell is cultured in the presence of a composition comprising an anti-CD3 antibody that is capable of providing a primary activation signal to a T cell and an anti-CD28 antibody that is capable of activating a co-stimulatory molecule on a T cell.

2. The method of claim 1, wherein the cell is genetically modified using a lentivirus expressing the oncogenic ALK.

3. The method of claim 1, wherein the cell exhibits one or more features of that of a corresponding tumor cell isolated from a human cancer having anaplastic large-cell lymphoma morphology.

* * * * *